(12) United States Patent
Okumura et al.

(10) Patent No.: US 6,947,516 B2
(45) Date of Patent: Sep. 20, 2005

(54) X-RAY CT APPARATUS

(75) Inventors: Miwa Okumura, Tochigi-ken (JP);
Masahiko Yamazaki, Tochigi-ken (JP);
Satoru Nakanishi, Tochigi-ken (JP);
Toshihiro Rifu, Tochigi-ken (JP); Souji Miyashita, Hokkaido (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 131 days.

(21) Appl. No.: 10/077,819

(22) Filed: Feb. 20, 2002

(65) Prior Publication Data

US 2002/0176530 A1 Nov. 28, 2002

(30) Foreign Application Priority Data

Apr. 4, 2001 (JP) .................................... P2001-105957

(51) Int. Cl.[7] .............................................. A61B 6/00
(52) U.S. Cl. ......................................... 378/19; 378/154
(58) Field of Search ............................ 378/4, 19, 98.8, 378/147, 149; 250/370.09, 505.1

(56) References Cited

U.S. PATENT DOCUMENTS

| | | | | |
|---|---|---|---|---|
| 5,131,021 A | * | 7/1992 | Gard et al. | 378/19 |
| 5,231,654 A | * | 7/1993 | Kwasnick et al. | 378/147 |
| 5,400,379 A | * | 3/1995 | Pfoh et al. | 378/19 |
| 6,028,908 A | | 2/2000 | Taguchi | |
| 6,304,626 B1 | * | 10/2001 | Adachi et al. | 378/19 |

FOREIGN PATENT DOCUMENTS

| JP | 6-169911 | 6/1994 |
|---|---|---|
| JP | 7-84052 | 3/1995 |

* cited by examiner

Primary Examiner—Edward J. Glick
Assistant Examiner—Courtney Thomas
(74) Attorney, Agent, or Firm—Oblon, Spivak, McClelland, Maier & Neustadt, P.C.

(57) ABSTRACT

An X-ray apparatus including an X-ray source, a rotation mechanism which rotates the X-ray source about a rotational axis, and an X-ray detector having a plurality of detection elements. A blocking member defining a slit structure is provided between the X-ray source and the X-ray detector. The slits of the blocking member include two rows aligned in a channel direction of the detection elements, and two rows staggered in the channel direction, thereby to obtain a CT image with improved spatial resolution. Alternatively, instead of using a blocking member, some of the detection elements of at least one detection segment are staggered in the channel direction with respect to detection elements of another detection segment.

7 Claims, 20 Drawing Sheets

(a)

(b)

SEG DIRECTION → CH DIRECTION (c)

(d)

(a)

(b)

(a)

(b)

(a)

(b)

(c)

(a)

(b)

(c)

(a)

(b)

X-RAY CT APPARATUS

CROSS-REFERENCE TO RELATED APPLICATIONS

This application claims priority under 35 U.S.C. § 119 to Japanese patent application No. P2001-105957 filed Apr. 4, 2001, the entire content of which are incorporated by reference herein.

BACKGROUND OF THE INVENTION

Computerized tomography (CT) has developed dramatically in recent years, and X-ray CT apparata in particular are rapidly taking their place as one of the most important medical diagnostic aids.

In these X-ray CT apparata, X-rays emitted from an X-ray tube permeate the subject of examination (generally the patient), and are converted into electric charges and thence into images by an X-ray detector including segments of detection elements.

However, the spatial resolution in X-ray CT apparata of this sort depends on the distance between adjacent detection elements in the detector. Thus, spatial resolution improves if both the size of the individual detection elements and the distance between them are minimized. Nevertheless, there is a limit to the extent to which the size of the detection elements can be reduced.

There is a method known as the quarter-quarter (QQ) method whereby spatial resolution can be improved without altering the size of the detection elements, which is to say without altering the distance between them. This is achieved by staggering the alignment-centered axis and the rotation-centered projection axis of the detector by a specified distance. It should be pointed out that what is called the rotation-centered axis runs through the rotational center of the detector and is roughly perpendicular to its rotational plane, while the detector rotation-centered projection axis is a line projecting the rotation-centered axis from the X-ray focal point along the detector. Meanwhile, the alignment-centered axis of the detector is such that the number of detection elements on the detector is the same in relation to that axis, which is roughly parallel to the rotation-centered axis.

To explain the QQ method in greater detail, the alignment-centered axis of the detector is staggered approximately ¼ the width of the detection element in relation to the rotation-centered projection axis. Thus, by making use of projection data detected at the prescribed angle (hereinafter referred to as 'principal data') and projection data detected when the detector is rotated approximately 180° from the prescribed angle (hereinafter referred to as 'QQ data'), it is possible to improve spatial resolution.

FIG. 1(a) illustrates the arrangement of detection elements on a detector used in the QQ method. For the purpose of this description it will be assumed that the detector has detection elements arranged one segment by four channels. It should be noted that by channel direction (CH direction) is meant the alignment of detection elements in a direction which is roughly perpendicular to the alignment-centered axis, while segment direction means a direction which is roughly parallel to the alignment-centered axis. The size of the detector in either direction is referred to respectively as channel width (CH width) and segment width.

Because the rotation-centered projection axis C' (denoted by a dotted line) of the detector is staggered by approximately ¼ CH width in the channel direction in relation to the alignment-centered axis C (denoted by an unbroken line), what is detected is projection data (QQ data) staggered by approximately ½ CH width in the channel direction in relation to the projection data (principal data) shown in FIG. 1(a), which is the standard. It should be noted that FIGS. 17(a) and (b) are as viewed from the same direction.

Since this QQ data is valuable as data from between the detection elements of principal data, combining (inserting) these two types of projection data makes it possible to obtain data with a resolution of approximately ½ channel width, as represented schematically in FIG. 1(c). This means that theoretically the spatial resolution improves roughly twofold as compared with when the QQ method is not applied.

A further development on the QQ method is represented by the technique described in Japanese Laid-Open Patent Application H7[1995]-84052. This technique involves staggering each detection element segment in the channel direction in a detector in which detection elements of two or four segments are aligned, thus allowing data to be collected simultaneously without rotating the data corresponding to QQ data through 180° with the principal data.

This technique again makes it possible to obtain a resolution which is theoretically twice that of a diagnostic image obtained without using the QQ method.

Yet another technique is one described in Japanese Laid-Open Patent Application H5[1994]-169911, according to which the detector has a three-segment detection element with each segment staggered by approximately ⅓ CH width in the channel direction. Moreover, the rotation-centered projection axis of the detector is staggered by approximately 1/12 CH in relation to the alignment-centered axis.

By making use of principal data in the three segments and QQ data corresponding to that principal data, this technique makes it possible to obtain a resolution which is theoretically some six times that of a diagnostic image obtained without using the QQ method.

Nevertheless, although by using principal data and QQ data the first and second conventional examples described above make it possible to obtain a resolution which is approximately twice that obtained without using the QQ method, there have been limitations to the extent to which this could be further improved. This means, for instance, that in clinical use it is difficult to observe diseases of the temporal bone in the field of otorhinology, diseases of the lung or fine blood vessels in the head (0.3 m), and in particular to distinguish between inflammation and cancer at the lobular level.

Moreover, while the third example cited above reportedly makes it possible to achieve approximately six times the resolution as compared with when the QQ method is not applied, there is no mention of how projection data for a prescribed slice surface is interpolated from the projection data obtained.

Apart from this there are no example of conventional methods in which detectors are provided with X-ray blocking members. X-ray blocking members serve to inhibit the X-ray transmission coefficient within a certain range of X-rays incident on the detection elements.

For instance, in the third example quoted above the images are reconstructed using X-rays detected in ⅙ the channel width of the detection elements. In other words, projection data is acquired with the remaining ⅚ of the channel width overlapping.

When there is a great deal of overlapping projection data, this leads to an indistinctness of image which in turn results in poorer resolution.

SUMMARY OF THE INVENTION

It is an object of the present invention to supply an X-ray CT apparatus and X-ray detector which will solve the above problems and make it possible to obtain a CT image with good spatial resolution.

In order to attain the above object, there is provided an X-ray CT apparatus according to one aspect of the present invention including an X-ray source configured to generate X-rays towards a subject, a rotation mechanism configured to rotate the X-ray source around a rotational axis, an X-ray detector having a plurality of detection elements arranged in a first direction roughly parallel to the rotational axis and in a second direction which is different from the first direction, which detect X-rays emitted from the X-ray source, a blocking member located between the X-ray source and the X-ray detector and configured to block X-rays, and a reconstruction unit configured to reconstruct an image of the subject in accordance with the data detected by the X-ray detector, wherein the blocking member has an aperture including a first section and a second section, the second section located in the first direction in relation to the first section and staggered in relation to the first section in the second direction.

According to another aspect of the present invention, there is provided an X-ray CT apparatus including an X-ray source configured to generate X-rays towards a subject, a rotation mechanism configured to rotate the X-ray source around a rotational axis, an X-ray detector having a plurality of detection elements arranged in a first direction roughly parallel to the rotational axis and in a second direction which is different from the first direction, which detect X-rays emitted from the X-ray source, and a reconstruction unit configured to reconstruct an image of the subject in accordance with the data detected by the X-ray detector, wherein the X-ray detector has at least four detection elements in the first direction, at least two detection elements being arranged aligned in relation to the second direction, and at least two detection elements which are staggered against the aforesaid at least two X-ray detection elements in relation to the second direction.

According to a further aspect of the present invention, there is provided an X-ray CT apparatus including an X-ray source configured to generate X-rays towards a subject, a rotation mechanism configured to rotate the X-ray source around a rotational axis, an X-ray detector having a plurality of detection elements arranged in a first direction roughly parallel to the rotational axis and in a second direction which is different from the first direction, which detect X-rays emitted from the X-ray source, a plurality of blocking members configured to block X-rays and arranged in the first and second directions respectively, and a reconstruction unit configured to reconstruct an image of the subject in accordance with the data detected by the X-ray detector, wherein the blocking members include first blocking members and second blocking members, the second blocking members located in the first direction in relation to the first blocking members and staggered in relation to the first blocking members in the second direction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 2:
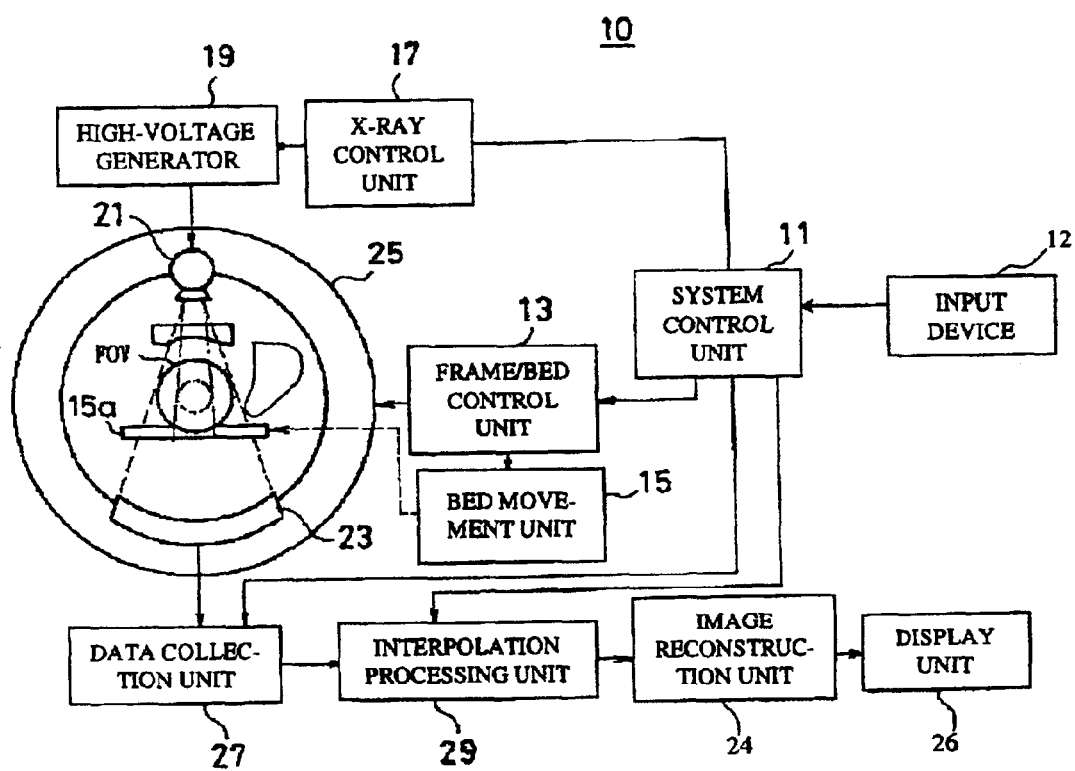
FIG. 2 is a system block diagram of the CT apparatus to which a first embodiment of the present invention pertains.

Referring now to the drawings, wherein like reference numerals designate identical or corresponding parts throughout the several views, FIG. 2 is a systematic structural diagram of the CT apparatus to which the first embodiment of the present invention pertains. As may be seen from FIG. 2, the X-ray CT apparatus 10 has a system control unit 11, an input device 12, a frame/bed control unit 13, a bed movement unit 15, a bed 15a, an X-ray control unit 17, a high-voltage generator 19, an X-ray beam generating source 21, a detector 23, a rotational frame 25, a data collection unit 27, an interpolation processing unit 29, an image reconstruction unit 24 and a display unit 26.

In the system control unit 11, a keyboard, mouse or other input device 12 is used to input the speed of rotation, slice thickness, fan angle and other data, which are output as a frame/bed control signal to the frame/bed control unit 13. The system control unit 11 also outputs to the X-ray control unit 17 an X-ray beam generation control signal which controls the generation of X-ray beams, and to the data collection unit 27 a detection control signal which indicates the timing for detecting X-ray beams. It also outputs to the data collection unit 27 a data collection control signal for data collection, and to the interpolation processing unit 29 an interpolation control signal which indicates the method of interpolation. The frame/bed control unit 13 not only allows the rotational frame 25 to rotate in accordance with the frame/bed control signal output from the system control unit 11, but also outputs a bed movement signal to the bed movement unit 15. The bed movement unit 15 determines the amount by which the bed 15a should move for each rotation of the rotational frame 25 in accordance with the bed movement signal output from the frame/bed control unit 13, and moves the bed 15a by this amount.

The X-ray control unit 17 controls the timing for the high-voltage generator to generate high voltage in accordance with the X-ray beam generation control signal output from the system control unit 11.

The high-voltage generator 19 supplies the X-ray beam generating source 21 with high voltage for emitting the X-ray beam in accordance with a control signal from the X-ray control unit. The X-ray beam generating source 21 emits the X-ray beam with the aid of the high voltage supplied from the high-voltage generator 19. The detector 23 a multi-slice detector which collects projection data penetrating the subject. This will be explained in detail later. The rotational frame holds the X-ray beam generating source 21 and the detector 23. Moreover, the rotational frame 25 can be rotated with the aid of a frame rotation mechanism (not depicted in the drawing) around an rotational axis (rotation-centered axis) which passes through the middle point between the X-ray beam generating source 21 and the detector 23.

The data collection unit 27 collects projection data detected by the detector 23 in response to a data collection control signal output from the system control unit 11. Moreover, the data collection unit 27 in the present embodiment has a switch function. This function makes it possible at the command of the operator to switch selectively between a mode employing the QQ method (QQ mode) and an ultra-high resolution mode employing a method (explained hereinafter) which is capable of providing an image of higher resolution than that of the QQ method. The interpolation processing unit 29 interpolates projection data on the desired slice position in accordance with projection data collected by the data collection unit 27. The interpolation processing unit 29 will be described in greater detail hereinafter. It should be added that hereinafter data detected by the detector 23 will be referred to as raw data, while that interpolated from the raw data will be referred to as interpolation data. The image reconstruction unit 24 reconstructs images in accordance with interpolation data generated by the interpolation processing unit 29. The display unit 26 displays images reconstructed by the image reconstruction unit 24 on a monitor (not depicted in the drawing).

There follows a description of the detector 23 with reference to FIGS. 3(a)–3(d). FIG. 3(a) is a front view of the detector 23 from the segment directions, while FIG. 3(b) is a front view of the support unit supporting the X-ray detection element and other elements; FIG. 3(c) is a front view of the slit structure as seen from the X-ray beam generating source; and FIG. 3(d) is a side cross-sectional view of the detector 23. In order to simplify the description, the support unit and slit structure have been illustrated separately.

The detector 23 is located on the X-ray beam generating source side of the support unit 39 which supports the detection unit 36, and has a slit structure 35 which blocks certain X-rays. The slit structure 35 and support unit 39 are fixed by passing a screw 34 through a screw hole 33 in the slit structure 35 and tightening it to a screw groove 33' in the support unit 39.

Viewed from the segment direction, the support unit 39 is roughly arc-shaped with a hollow inside. Within the support unit 39 is the detection unit 36 and a collimator 37 on the X-ray beam generating source side thereof.

On the detection unit 36 are arranged the detection elements 32, including 34 segments by 900 channels (shown by respective arrows). The positions of the segments of detection elements tally in both segment and channel directions with the adjoining segment, which is to say they are not staggered.

The center four segments of detection elements are each 0.5 mm wide. The 15 segments extending in the segment direction of the center four segments of detection elements and the 15 segments extending in the opposite direction (a total of 30 segments) are each 1 mm wide. As far as channel width is concerned, all the detection elements are the same length. For the sake of simplicity, FIG. 3(b) depicts only four segments of detection elements of 0.5 mm width and four of 1 mm width.

The slit structure 35 is, like the support unit 39, roughly arc-shaped when viewed from the segment direction, and comprises an X-ray blocking member with a low X-ray transmission coefficient. The slit structure 35 has a plurality of slits 31 which penetrate from the X-ray beam generating source side in the direction of the support unit 39. The X-ray transmission coefficient of the X-ray blocking member is for instance about 20% or less.

The slits 31 are located within the width of roughly the 700 channels nearest the center of the detection element.

There next follows an explanation of the shape and positions of the slits 31.

The slits 31 are roughly oblong in shape, the width in the channel direction being about one-half the channel width of the detection element 32, while that in the segment direction is the same as that of the detection unit 26 in the segment direction. To be more precise, out of an area of about four segments in width (taking each segment to be 0.5 mm wide) in the central section of the detection element, an area two segments in width is staggered by a prescribed distance in the channel direction, while the remaining area two segments in width is staggered in the opposite direction. This will be explained in greater detail below.

The position of the slits 31 in the segment direction tallies with the position of the detection unit 36. The position of the slits 31 in the segment direction will be explained in greater detail below.

The slits 31 are positioned equidistantly at a width of one channel each of the detection element in the channel direction.

Figure 3:
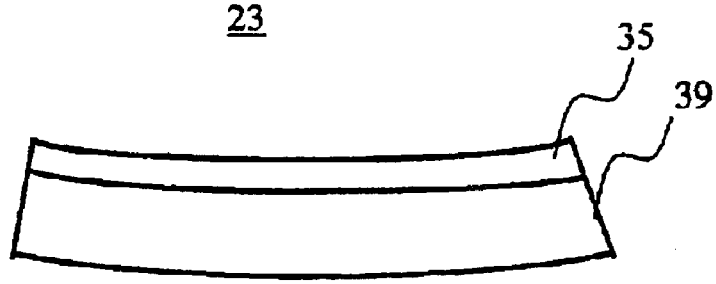
FIGS. 3(a)–3(d) are top, front and side views illustrating the detector to which the first embodiment of the present invention pertains as viewed from the X-ray beam generating source.
Figure 3:
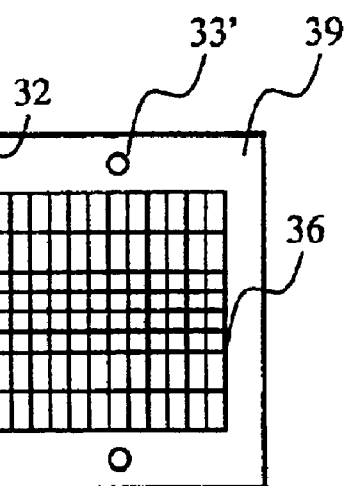
Figure 3:
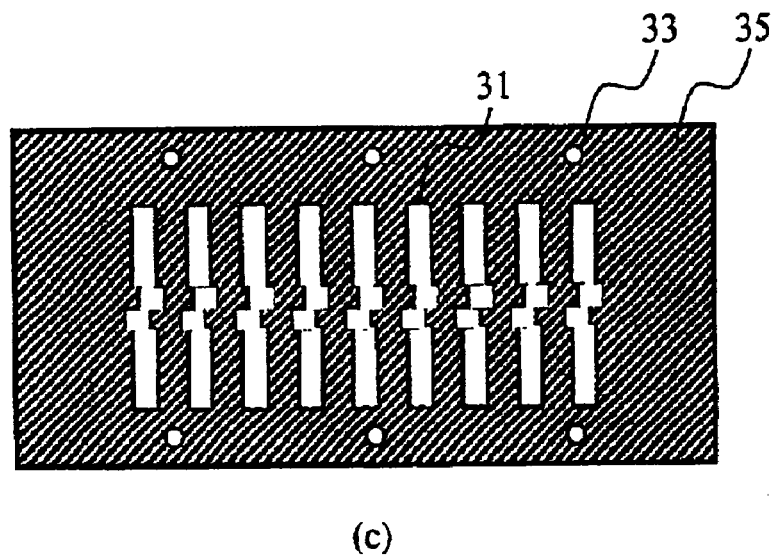
Figure 3:
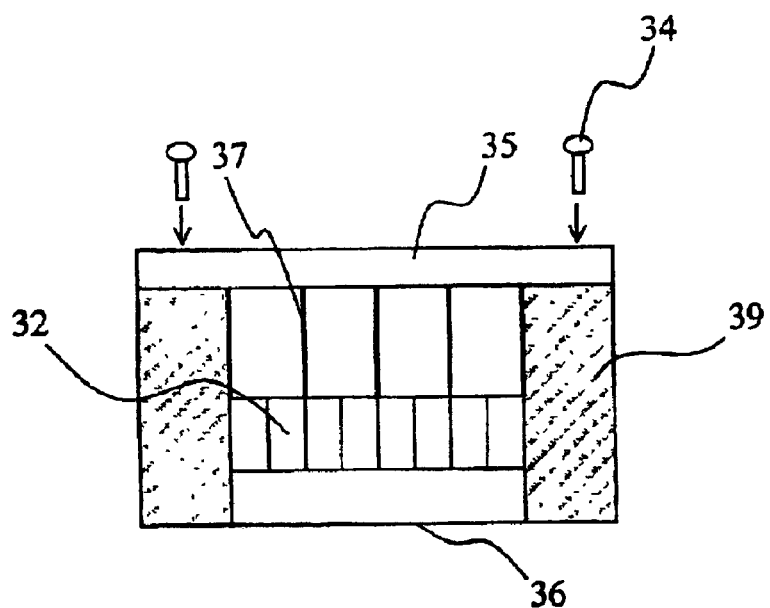
Figure 4:
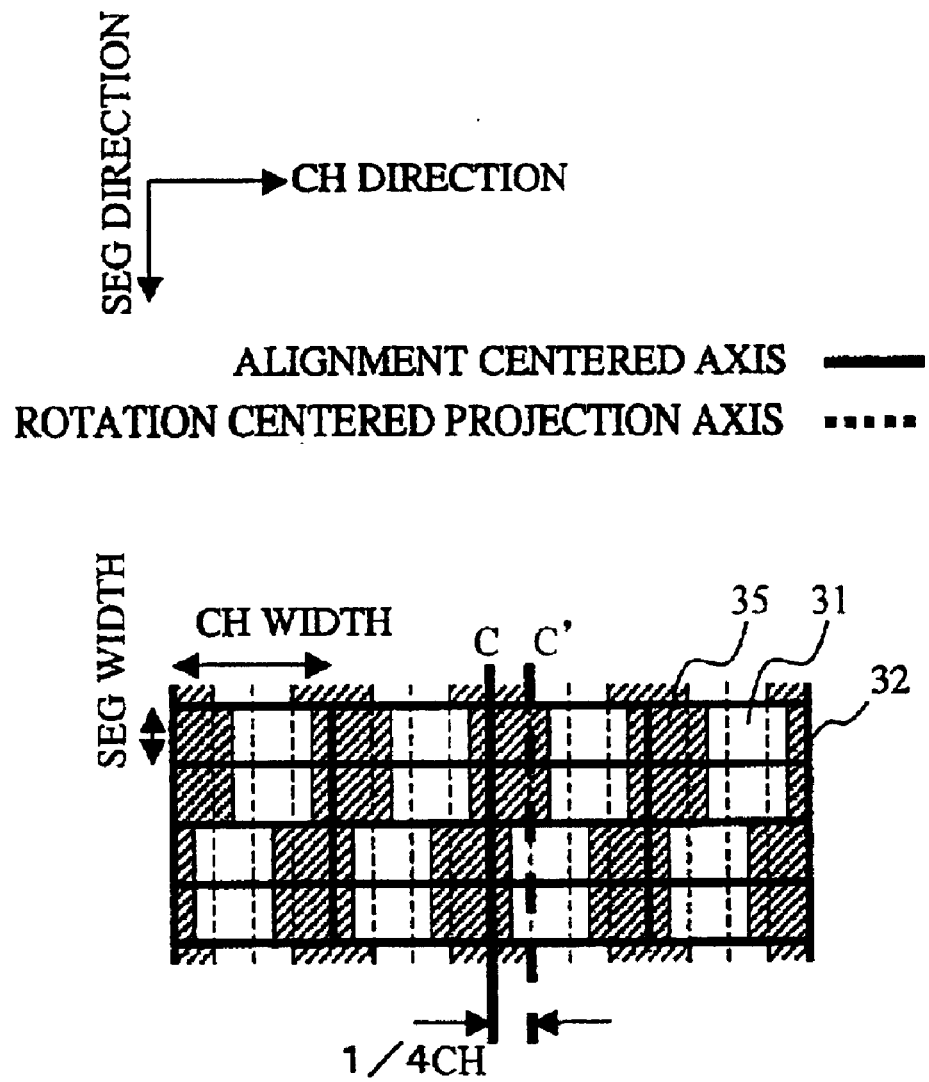
FIG. 4 is a top view in the vicinity of the center of the detector to which the first embodiment of the present invention pertains as viewed from the X-ray beam generating source.

There follows, with reference to FIGS. 3(a)–(d) and 4, a detailed description of the slits 31 located on the four segments of detection element nearest the center (each segment being 0.5 mm in width). FIG. 4 is a top view (four segments by four channels) in the vicinity of the center of the detector to which the first embodiment of the present invention pertains as viewed from the X-ray beam generating source, while FIG. 5 is a partially enlarged top view of a detection element.

It should be noted that in FIGS. 3 and 4 the position and size of the slits 31 in relation to the detection element 32 have for the sake of clarity been shown by a dotted line. This dotted line has been shown in a position approximately ¼ channel. The slit structure 35 has been shown with oblique shading.

Figure 5:
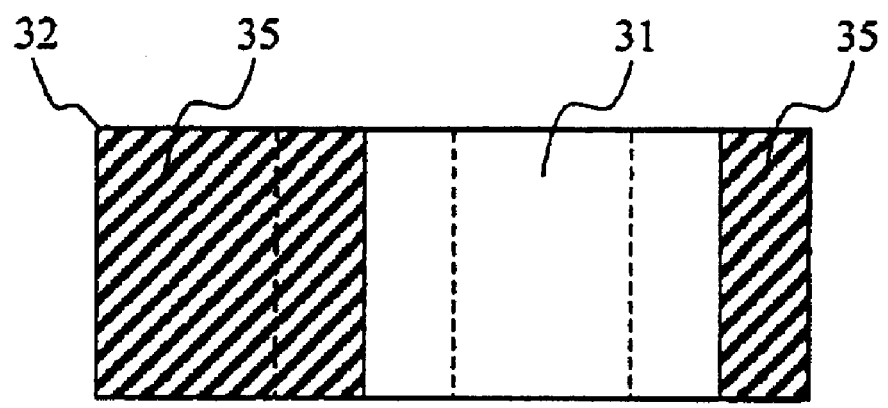
FIG. 5 is a partially enlarged top view of a single detection element in the first embodiment of the present invention.

FIG. 5 illustrates the detection element 32 which corresponds to the top two segments of the four-segment detection element at the center of FIG. 4. As may be seen from FIG. 5, the connection between the detection element 32 and the slit 31 is such that there is a slit roughly one-half of a channel in width centered on a position staggered by the width of about ⅛ channel in the channel direction from the center of the detection element 32.

Meanwhile, there is a slit 31 roughly one-half of a channel in width centered on a position staggered by the width of about ⅛ channel in the channel direction from the center of the detection element 32 and corresponding to each detection element 32 in the bottom two segments.

In other words, the slits 31 are arranged in such a manner that the slit of each detection element in the top two segments is staggered in the channel direction by the width of approximately ¼ channel in relation to the slit of each detection element in the bottom two segments.

Figure 7:
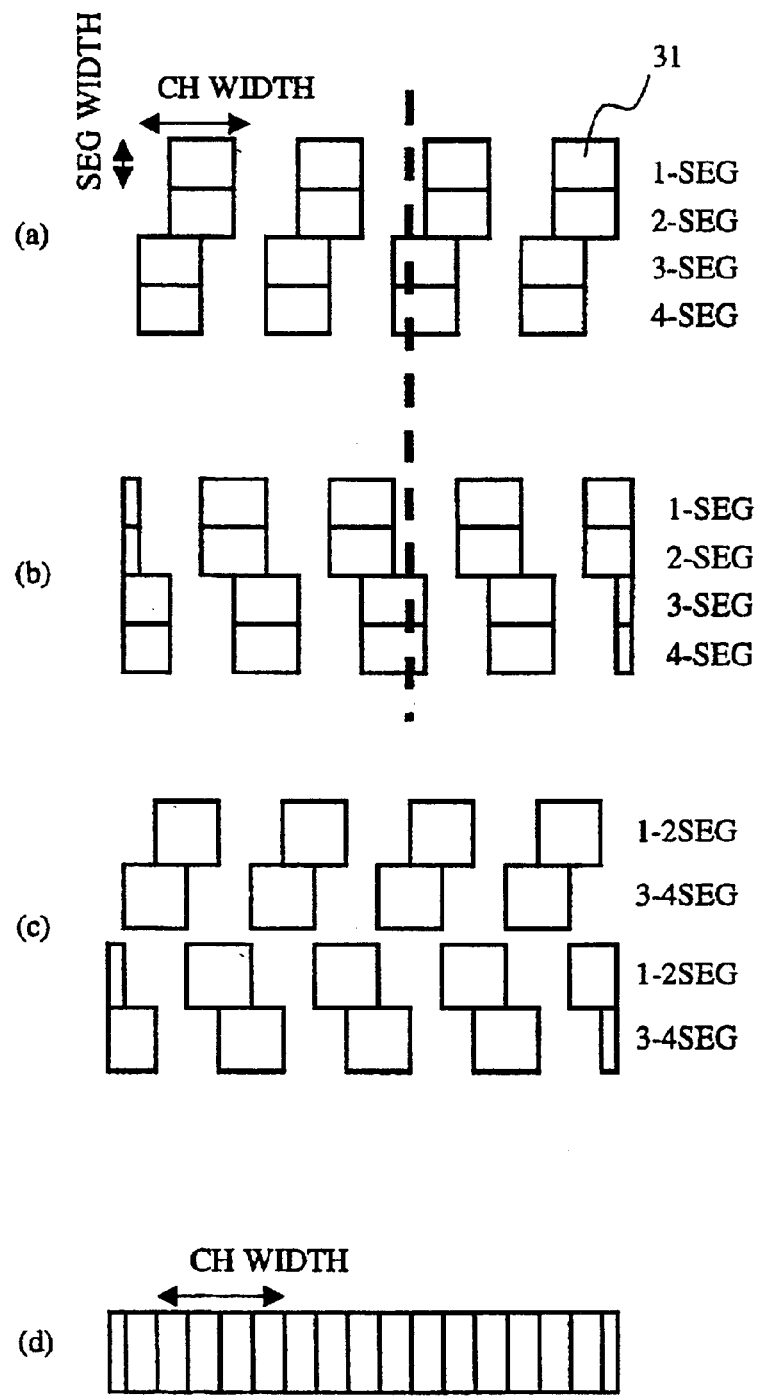
FIGS. 7(a)–7(d) are schematic illustrations illustrating the detector slit and interpolation data in the first embodiment of the present invention.

Moreover, the slits in the top two segments in the drawing are staggered in the channel direction by the width of approximately ⅛ channel in relation to the slits in the other 30 segments of detection elements of the detection unit 36, while those in the bottom two segments are staggered in the opposite direction by the width of approximately ⅛ channel. FIG. 7(a) shows the slits 31 of only the middle four segments.

FIG. 4 shows the alignment-centered axis C (unbroken line) and the rotation-centered projection axis C' (broken line) of the detector 23. The four-segment-by-four-channel detection element 32 at the center of the detection unit 36 is arranged in two groups of four segments by two channels symmetrically in relation to the alignment-centered axis of the detector 23.

The rotation-centered projection axis C' of the detector 23 is staggered by the width of approximately ¼ channel in relation to the alignment-centered axis C.

Figure 6:
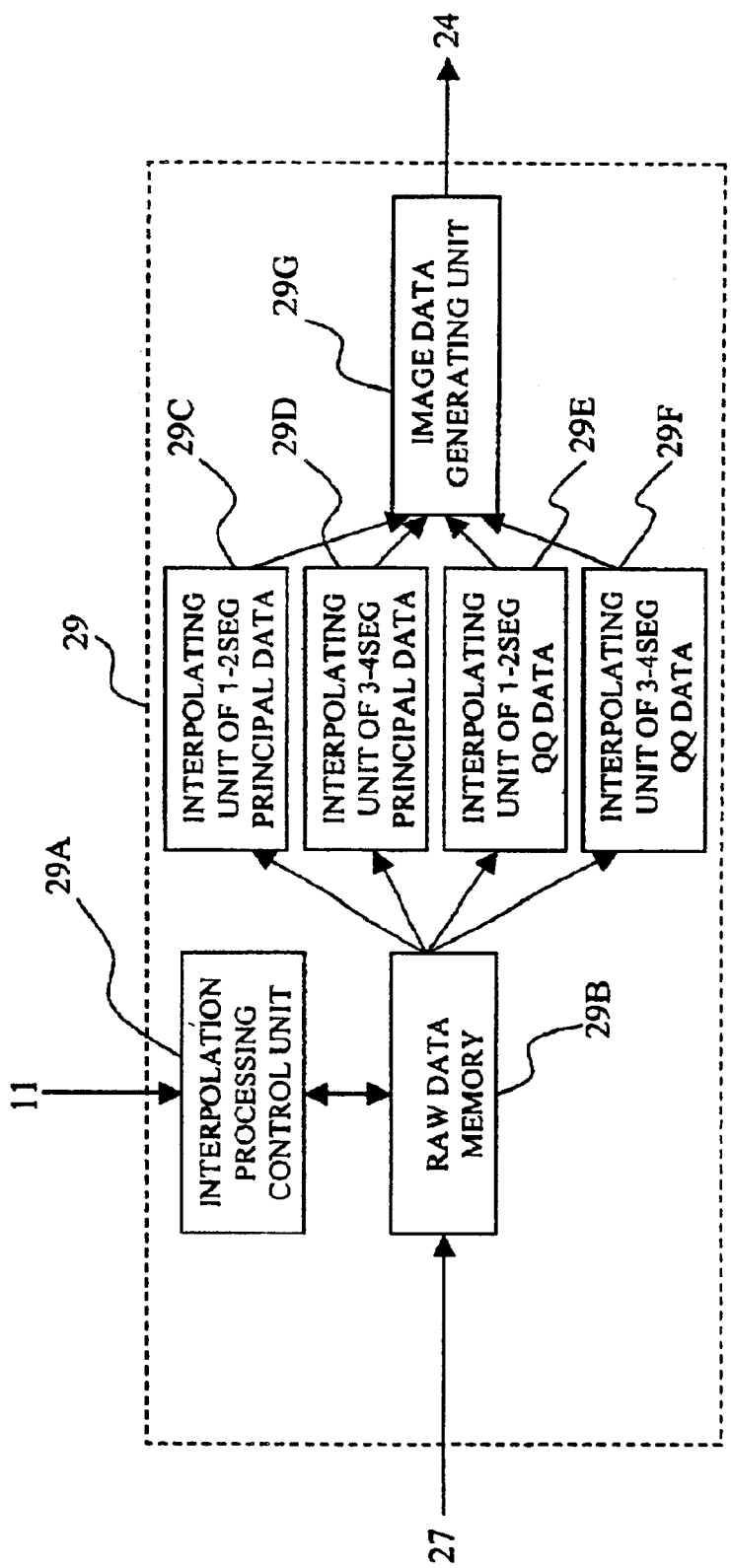
FIG. 6 is a detailed block diagram illustrating an interpolation processor in the first embodiment of the present invention.

There follows, with reference to FIG. 6, a detailed description of the interpolation processing unit 29. FIG. 6 is a block diagram illustrating only that part of the interpolation processing of FIG. 2 which is used in ultra-high resolution mode. The interpolation processing unit employed in QQ mode has been omitted.

The interpolation processing unit 29 has an interpolation processing control unit 29A, a raw data memory unit 29B, a unit 29C for interpolating principal data between segments 1 and 2, a unit 29D for interpolating principal data between segments 3 and 4, a unit 29E for interpolating QQ data between segments 1 and 2, a unit 29F for interpolating QQ data between segments 3 and 4, and an image data generating unit 29G.

The interpolation processing control unit 29A outputs an interpolation processing control signal to be input from the system control unit 11, and outputs a control signal to be read into the raw data memory unit 29B which stores raw data. The raw data memory unit 29B stores raw data input from the data collection unit 27, and outputs it to each of the data interpolation units 29C–29F.

Interpolation data interpolated in the data interpolation units 29C–29F is output to the image data generating unit 29G, and the output of the image data generating unit 29G is input to the image reconstruction unit 24.

There now follows an explanation of the action of the present embodiment, which is divided into (1) outline CT action, (2) detailed action of the detector and data collection unit, and (3) detailed action of the interpolation processing unit.

(1) Outline CT Action (cf. Principally FIGS. 1(a)–1(c))

Figure 1:
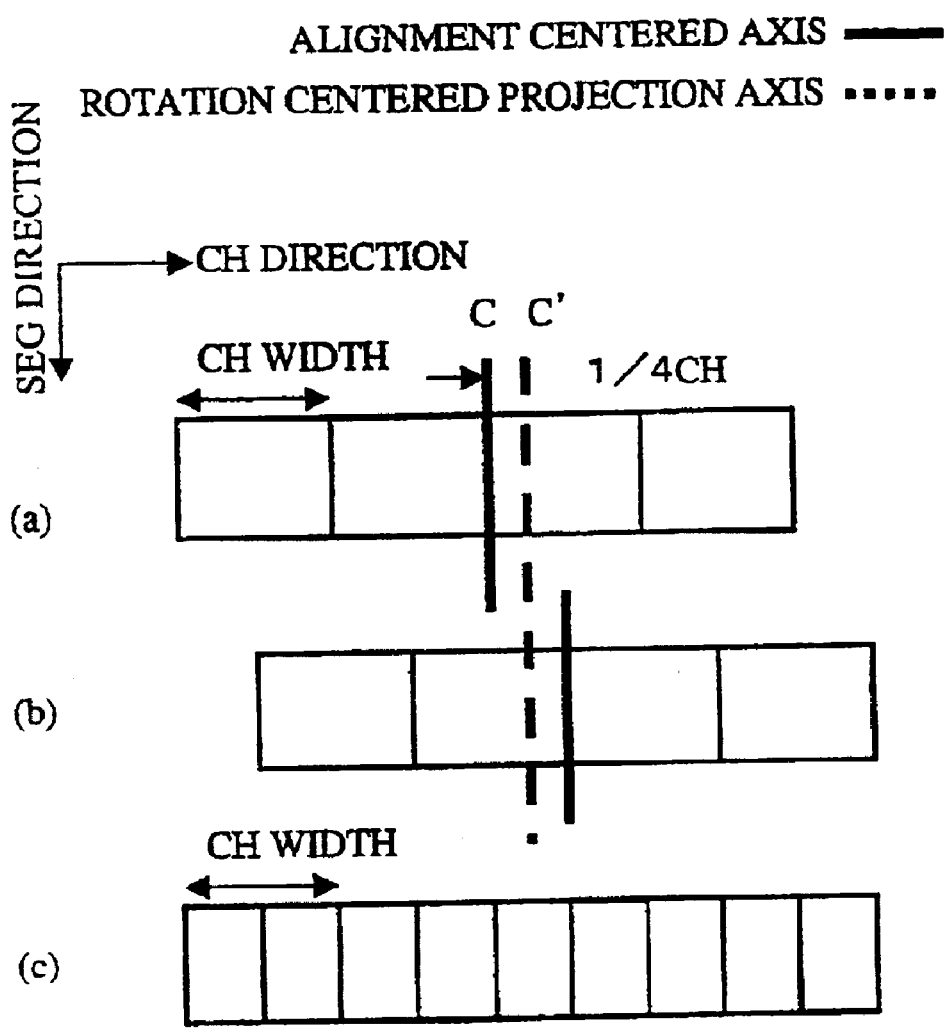
FIGS. 1(a)–1(c) are schematic illustrations of an arrangement of detection elements in a conventional detector.

In FIG. 1, the operator uses the input device 12 to input the conditions for scanning an area of interest. The following is an example of scanning conditions.

| Method of scanning | Helical scanning |
| (Helical pitch) | 2 |
| Number of detector segments used | N seg = 4 segments |
| Number of detector channels used | N ch = 700 channels |
| Mode | Ultra-high resolution mode |

The method of scanning may be for instance helical or conventional, and refers to the type of trajectory which the detector 23 describes when moving in relation to the area of interest. For example, helical scanning means that the detector 23 describes a helical trajectory in relation to the area of interest. The selections may include dynamic scanning and other methods of scanning apart from those mentioned above.

In the case of helical scanning in particular, the helical pitch is also set. This is a value which denotes the amount of relative movement of the area of interest and detector in the direction of the body axis during one rotation. For the purpose of the present embodiment it will be assumed that the helical pitch is 2. The helical pitch denotes the number of segment widths which the detector moves in the segment direction during a single rotation. The number of detector segments used is a condition for determining how many of the detector element segments are used. It is possible to use all the available segments (eg 34 segments), or just some of them. In the present embodiment, the number of detector segments used, mseg=4. Similarly, the number of detector channels used is a condition for determining how many of the detector element channels are used. It is possible to use all the available channels (eg 900 channels), or just some of them. In the present embodiment, the number of detector channels used, mch=700.

As explained above, operating modes include QQ mode and high-resolution mode. The explanation which follows assumes that high-resolution mode has been selected.

When the scanning conditions have been input, the system control unit 11 illustrated in FIG. 2 outputs the scanning mode, detector rotation speed, area of interest, slice thickness and other conditions in the form of a frame/bed control signal to the frame/bed control unit 13. In accordance with the frame/bed control signal, the frame/bed control unit 13 outputs a bed movement signal to the bed movement unit 15.

When now the operator inputs a bed start command from the input device, the system control unit 11 outputs an X-ray beam generating control signal to the X-ray control unit 17, commanding that scanning commence and an X-ray beam be generated. In response to the X-ray beam generating control signal, the X-ray control unit 17 generates high voltage from the high voltage generator 19.

As a result, an X-ray beam is emitted from the X-ray beam generating source 21, the bed 15a is moved by the bed movement unit 15, and helical scanning commences.

When a data collection control signal (including number of detector segments used, number of channels used and other scanning conditions is output from the system control unit 11, in response the data collection unit 27 collects X-rays detected by the detector 23 as projection data and supplies them to the interpolation processing unit 29. The actions of the detector 23 and data collection unit 27 will be described later.

When the X-ray beam is supplied, the interpolation processing unit 29 interpolates an X-ray beam in the position of the desired slice in accordance with this X-ray beam. The action of the interpolation processing unit 29 will be explained later.

The interpolation data interpolated by the interpolation processing unit 29 is reconstructed by the image reconstruction unit 24, and the reconstructed image is displayed on the display unit 26.

(2) Actions of the Detector and Data Collection Unit (cf. Principally FIGS. 2, 3(a)–3(d), 6 and 7(a)–7(d))

The X-ray generated by the X-ray beam generating source 21 permeates the subject of examination and becomes incident on the slit structure 35 of the detector 23 in FIG. 3. The slit structure 35 has a low X-ray transmission coefficient, but the X-ray which is incident on slits is not blocked by the slit structure and becomes incident on the collimator 37 behind it. Only X-rays from a specified direction pass through the collimator 37 and become incident on the detection unit 36 behind the collimator 37. In the detection unit 36, incident X-rays are converted by the X-ray detection element 32 into electric charges.

The electric charges converted from X-rays by the detection unit 36, are collected by the data collection unit 27 as projection data in accordance with a data collection control signal from the system control unit 11 and according to a specified timing whereby the signals of those electric charges which have been converted by a specified number (number of segments×number of channels) of detection elements 32 in specified positions on the detector 23 number are collected.

If the operator selects the high-resolution mode, the projection data collected by the data collection unit 27 is only that detected by the four center detection element segments (segment width 0.5 mm). If the operator selects QQ mode, projection data from other detection element segments (segment width 1 mm) in addition to or instead of the four center detection element segments is collected. The explanation which follows assumes that high-resolution mode has been selected.

The projection data is output as raw data to the interpolation processing unit 29. This raw data will be described in greater detail with reference to FIGS. 6(a), 6(b) and 7(a), 7(b). FIGS. 7(a)–7(d) are explanatory of the detector slit 31 and interpolation data, while FIGS. 8(a)–8(b) illustrates the collection route for projection data.

In FIG. 7(a), the position of the slit 31 when the detector 23 has rotated through a prescribed angle is shown. QQ data relative to projection data (principal data) detected by the slit 31 in this position is detected as symmetrical projection data around the detector rotation-centered axis C' as shown in FIG. 7(b).

In other words, raw data includes both principal data and QQ data relative to principal data, except that depending on the timing of reading data from the detector it may not always be possible to acquire projection data from a position wherein the detector has rotated 180° in relation to the position where the principal data was acquired. In such a case QQ data may be determined by interpolating raw data for both.

Figure 8:
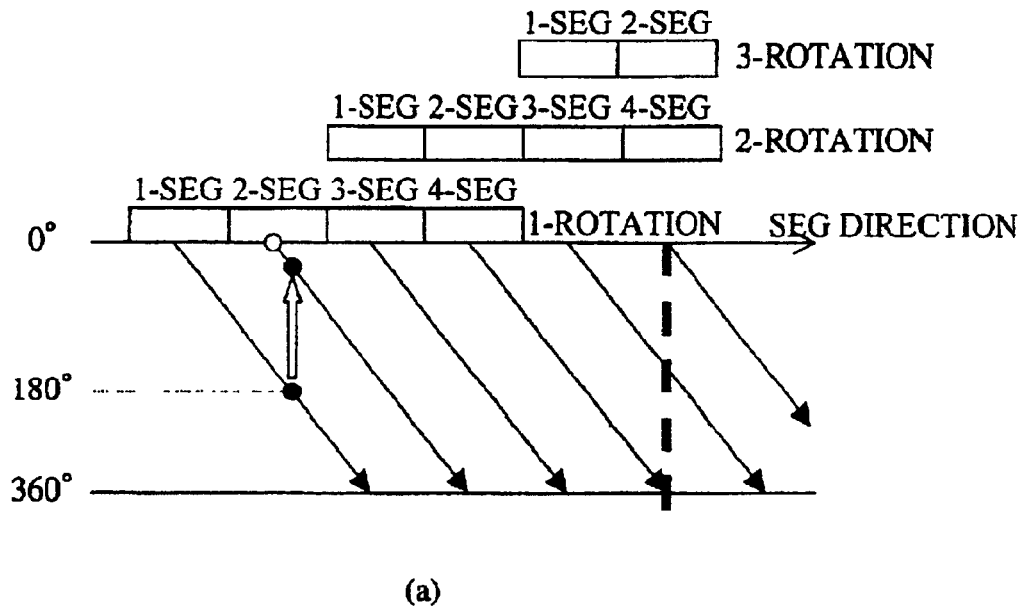
FIGS. 8(a)–8(b) are diagrams illustrating the collection route for projection data in the first embodiment of the present invention.
Figure 8:
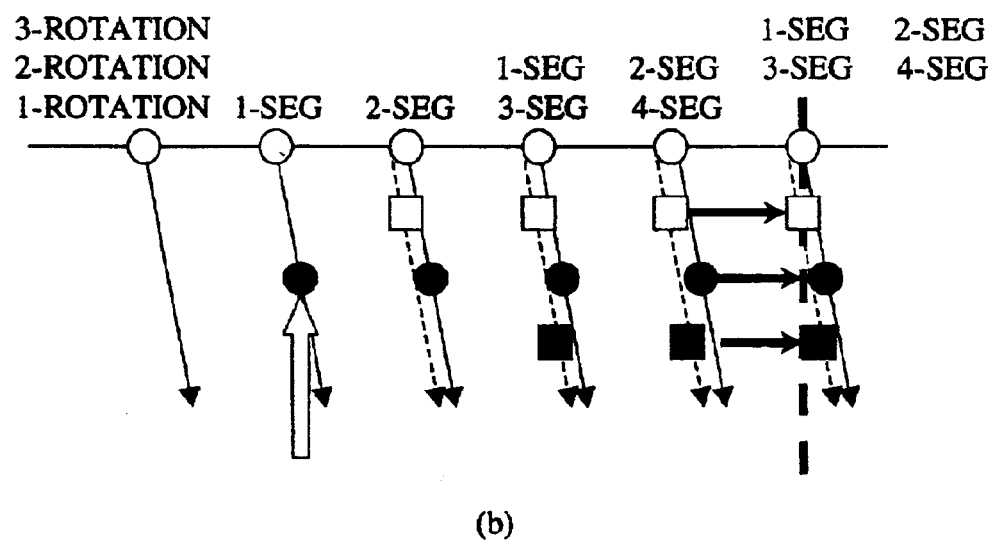

As FIG. 8(a) shows, in order to scan helically in the present embodiment with the helical pitch at 2 and taking the first to third rotations as an example, the third segment detection elements on the first rotation must describe more or less the same trajectory as those of the first segment on the second rotation, the fourth segment detection elements on the first rotation the same as those of the second segment on the second rotation, the third segment detection elements on the second rotation the same as those of the first segment on the third rotation, and the fourth segment detection elements on the second rotation the same as those of the second segment on the third rotation. It should be added that in FIG. 8(a) the oblique arrows represent the trajectories of the detection elements, the vertical axis the projection angle, and the horizontal axis the distance in the segment direction.

(3) Action of the Interpolation Processing Unit

There follows, with reference to FIGS. 5, 6 and 7(a)–7(d), a description of interpolation processing in the present embodiment.

Projection data collected in the data collection unit 27 described above is stored in the raw data memory unit 29B shown in FIG. 6. This raw data includes principal data as described above, and QQ data.

Into the interpolation processing control unit 29A are input interpolation processing control signal from the system control unit 11. These interpolation processing control signals include information such as helical pitch and slice position of images reconstructed in the image reconstruction unit.

There follows a description which is based on the assumption that, as indicated by the dotted line in FIGS. 8(a)–8(b), the slice position is in a position where the fourth segment detection elements are when the detector 23 is at 0° on the second rotation.

The interpolation processing control unit 29A selects the necessary raw data from among that stored in the raw data memory 29B, and outputs the selected raw data to the unit 29C for interpolating principal data between segments 1 and 2, the unit 29D for interpolating principal data between segments 3 and 4, the unit 29E for interpolating QQ data between segments 1 and 2, and the unit 29F for interpolating QQ data between segments 3 and 4.

The selection of this necessary raw data will be explained with reference to FIG. 8(b) which illustrates a portion of the slice surface (depicted with a dotted line) shown in FIG. 8(a) in the vicinity of 0°. Here the projection data represented by a circle is projection data detected by the first or second segment detection elements, while that represented by a square is projection data detected by the third or fourth segment detection elements. Unshaded raw data is principal data, while shaded raw data is QQ data. It should be noted that the vertical axis in FIGS. 8(a)–8(b) denotes the projection angle, and data of this sort is treated as the same projection data, so that strictly speaking it should be arranged in a perpendicular direction to the paper. It has been shown as staggered in the projection angle direction for the sake of convenience.

The relationship between principal data and QQ data is such that QQ data is projection data detected at a position wherein the angle of the detector is staggered by approximately 180° in relation to principal data. To be more precise, suppose that the principal data is projection data detected by the second segment detection elements at 0° on the first rotation (represented by a white dot). The QQ data is projection data detected by the first segment detection elements in the vicinity of 180° on the first rotation (represented by a black dot). Insertion means doubling the number of samplings by regarding QQ data as projection data detected at a position staggered in the channel direction in relation to the principal data. If insertion were to be depicted conceptually using FIG. 8(a), it is like copying projection data detected at a projection angle of roughly 180° to the vicinity of 0°, as shown by the white arrow.

Because the projection data detected by the first or second segment detection elements and that detected by the third or fourth segment detection elements are staggered in the channel direction, they are represented with different projection angles in FIGS. 8(a)–8(b). The collection route of the projection data detected by the third or fourth segment detection elements is represented with dotted arrows.

Accordingly, since the principal data detected by the first or second segment detection elements and that detected by the third or fourth segment detection elements along with the respective QQ data are each staggered in the channel direction, the number of samplings becomes fourfold. A line which joins an area where each detection element detects X-rays at the same projection angle and the X-ray beam generating source is an X-ray route. In other words, because in the present embodiment data detected by the first (or second) segment detection elements and data detected by the third (or fourth) segment detection elements can detect data staggered in the channel direction at the same projection angle, two X-ray routes exist.

The data required to create interpolation data at the projection angle 0° on the slice surface shown with a dotted line within the range illustrated in FIG. 8(b) in the relationship between principal data and QQ data is represented in FIG. 8(b) by black arrows, and is principal data from the first and second segments on the third rotation (white arrows), principal data from the third and fourth segments on the second rotation (white squares), QQ data from the second segment on the second rotation and first segment on the third rotation (black dots), and QQ data from the fourth segment on the first rotation and third segment on the second rotation (black squares).

In other words, of the raw data the projection data nearest and next nearest the slice surface is selected. The method of interpolating slice surface data using projection data detected on both sides of the segment direction with the slice surface between is called the external interpolation method. Meanwhile, the method of interpolating the slice surface data using projection data from one side only is called the internal interpolation method.

In order to create interpolation data it is necessary to have segments ½ principal data interpolation data, segments ¾ principal data interpolation data, segments ½ QQ data interpolation data and segments ¾ QQ data interpolation data.

This is created in the data interpolation units 29C to 29F in FIG. 6, and the concept is illustrated in FIG. 7(c).

The interpolation data created on the data interpolation units 29C to 29F form a collection of projection data to reconstruct the same slice surface with the aid of the image data generating unit 29G, and this is output to the image reconstruction unit 24 shown in FIG. 1.

FIG. 7(d) illustrates conceptually the output of the image data generating unit 29G. The various interpolation data in FIG. 7(c) have been gathered into a single data collection. As will be seen, it has ¼ resolution in relation to channel width.

The image reconstruction unit 24 reconstructs a single image from the projection data collection and generates a reconstruction image.

As has been explained above, the present embodiment makes it possible to provide a high-resolution CT image by staggering the slits by roughly ¼ channel width, and in addition staggering the detector rotation-center projection axis C' by roughly ¼ channel width in the channel direction in relation to the detector alignment-center axis. Moreover, the present embodiment makes it possible to interpolate internally between projection data which are shorter in the segment direction (one segment width in the present embodiment) than the slice pitch (2 in the present embodiment).

In the present embodiment, the slits in the slit structure are provided in different positions in the center four segment detection elements than in other segments. This means that in high-resolution mode it is possible to create images using projection data detected at a detection element segment width of 0.5 mm, and in QQ mode using projection data detected at a detection element segment width of 1.0 mm (virtually bundling 0.5 mm segment widths into 1 mm segments).

In other words, if image resolution is high in the segment direction (detection elements with small segment widths are used), it is possible to increase resolution in the channel direction. Meanwhile, it is also possible to decrease resolution in the channel direction if resolution in the segment direction is decreased (if it is desired to use a large segment width detection element to create an image with a broad range in the body axis direction). Thus in either mode it is possible to minimize the difference in resolution between the segment and channel directions.

Moreover, the use of X-ray blocking members to minimise the area which a single detection element is capable of detecting means that it is possible to reduce overlap of principal and QQ data, and to supply a clearer image.

There is also the advantage of ease of manufacture which results from the provision of a plurality of slits in a single slit structure.

Furthermore, in the above embodiment the slit structure 35 is fixed to the support unit 39 by means of a screw 34, but by providing a groove in the support unit 39 and fitting the slit structure in such a manner as to slide in the groove, it is possible to make use of replaceable slit structures with difference slit configurations. The availability of slits of different sizes and in differing positions makes if possible to select the resolution according to each diagnosis.

Figure 9:
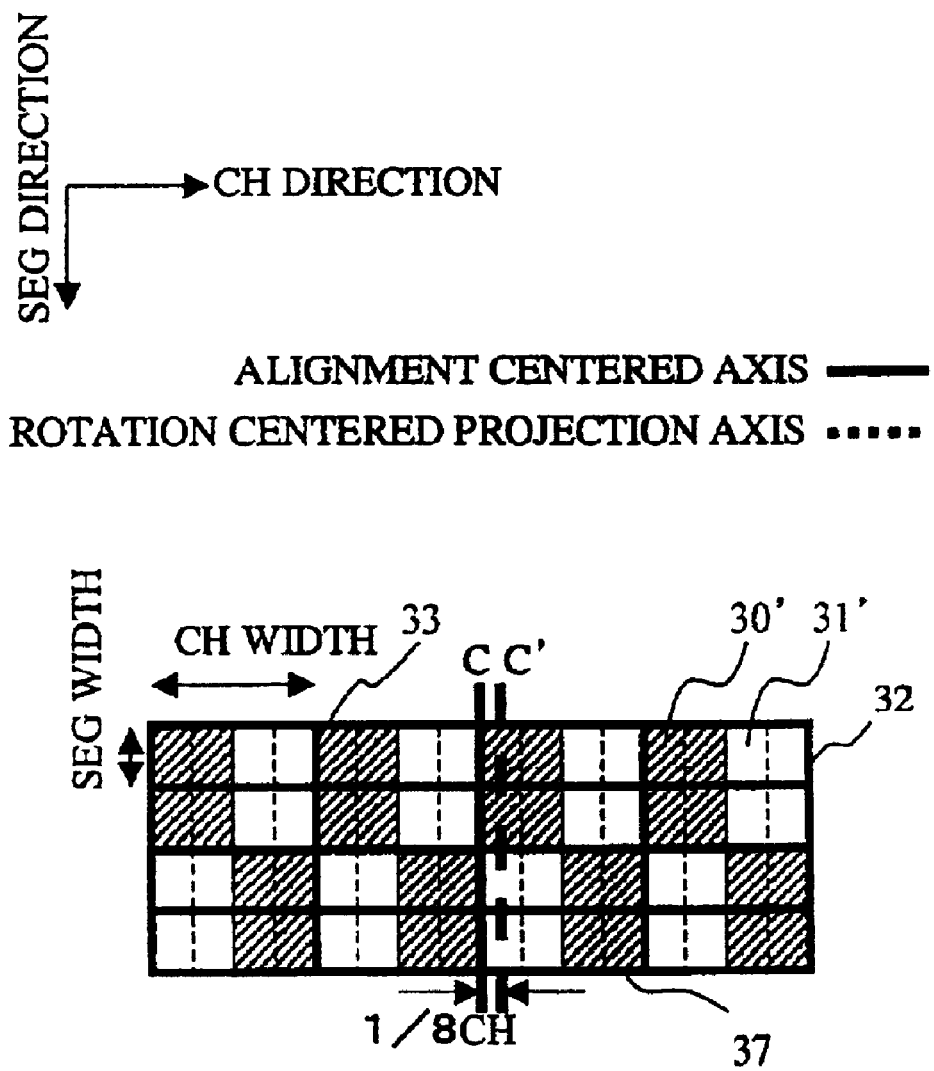
FIG. 9 is a top view in the vicinity of the center of the detector to which a first modification of the present invention pertains as viewed from the X-ray beam generating source.

There follow a description of a first modification to the present embodiment. This modification relates to the position of the slits in the segment direction. FIG. 9 is a top view in the vicinity of the center of the detector (four segments by four channels) to which the first modification of the present invention pertains as viewed from the X-ray beam generating source. Those parts of the configuration which are the same as in the first embodiment have been allocated the same reference numeral designations, and will not be explained again.

Figure 10:
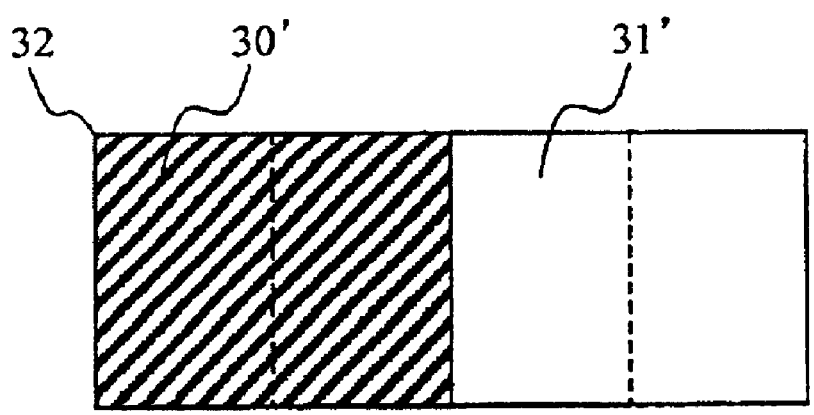
FIG. 10 is a partially enlarged top view of a single detection element in the first modification of the present invention.

As may be seen from FIG. 10, the slit structure 35' in this modification is divided into half-channel widths from the center of the detection element 32. In other words, in half of the detection elements 32 from the center thereof the X-rays are blocked by the slit structure 35', while they can be detected in the other hand (slit 31').

Moreover, as FIG. 9 shows, the positional relationship between the alignment-centered axis C (unbroken line) of the detector 23 and its rotation-centered axis C' is such that the alignment-centered axis C is staggered by approximately ⅛ channel width in relation to the rotation-centered axis C'.

Otherwise the configuration and action are roughly the same as in the first embodiment.

This modification also makes it possible to supply a high-resolution CT image as in the first embodiment.

There follow a description of a second modification to the present embodiment. This modification relates to the position and size of the slits in relation to the whole of the detector.

Figure 11:
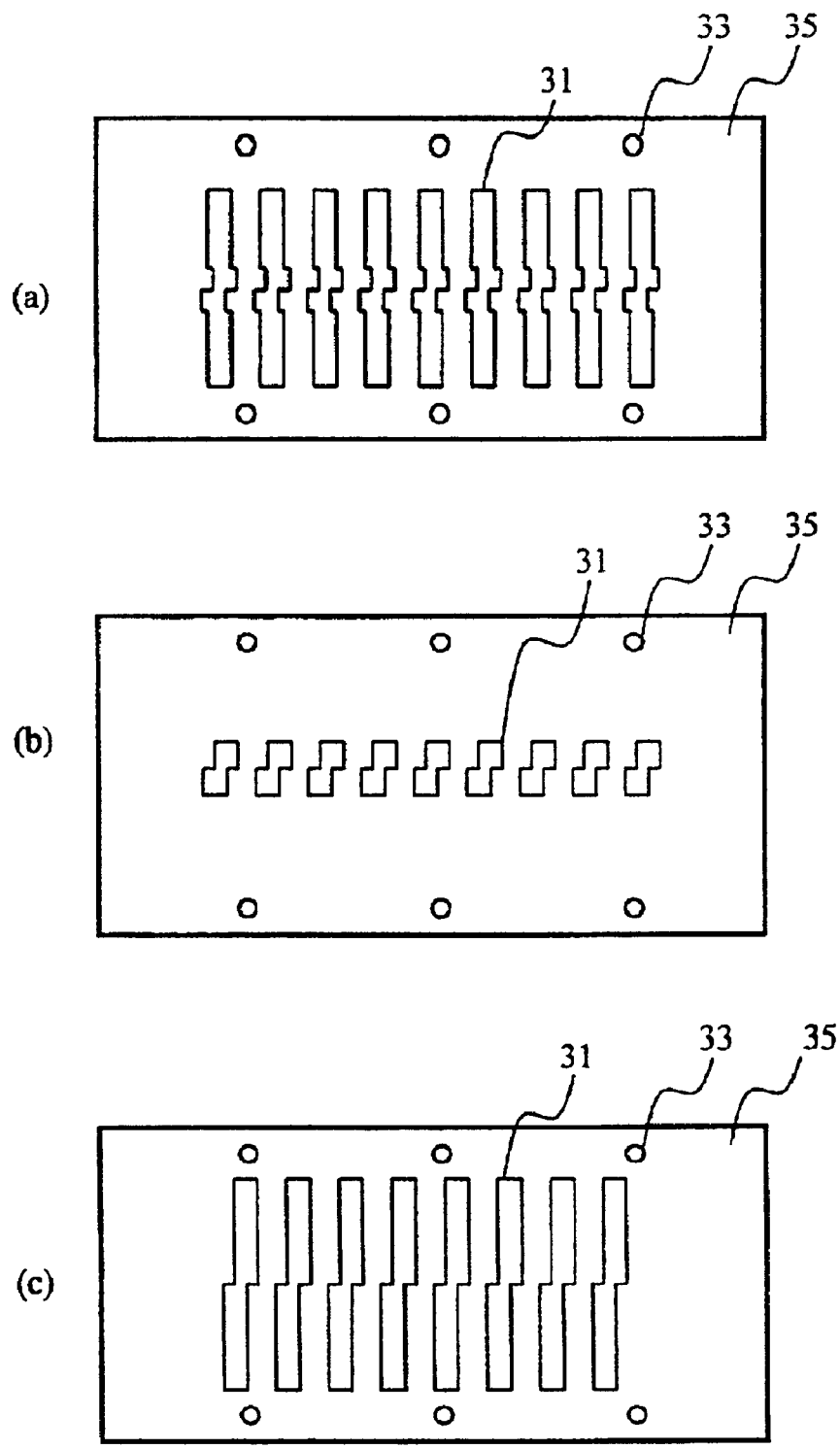
FIGS. 11(a)–11(c) are top views of a detector slit as viewed from the X-ray beam generating source in a second modification of the present invention.

FIGS. 11(a)–11(c) illustrates a modification of the slit 31 in the slit structure 35 of the present modification. It should be noted that the slit structure 35 illustrated in FIG. 11(a) is the same as that of the first embodiment. As FIG. 11(b) shows, it is possible with the slits in the first embodiment to have them only in areas where they are positioned on four-segment detection elements and not elsewhere. This could be thought of a slit structure for dedicated use in high-resolution diagnosis using only 0.5 mm segment width detection elements.

FIG. 11(c) shows an example where, in contrast to FIG. 11(b), slits are provided only in areas where they are positioned on four-segment detection elements but also elsewhere. It is the same as the example illustrated in FIG. 11(b) in that the slits are divided in the vicinity of the center into approximately ½ channel widths in the channel direction.

Using four-segment detection elements not only in the center but also elsewhere in this manner makes it possible to create high-resolution images.

It is also possible to change the number of slits 31. For instance, by increasing the number of slits and using all 900 channels of detection elements it is possible to take a broad area of interest in the body axis direction and roughly vertical surface.

On the other hand it is also possible to reduce the number of slits. For instance, if there are slits on only 400 channels of detection elements, the area of interest in the body axis direction and roughly vertical surface is small, and the number of projection data can be reduced.

In other words, the number of slits 31 can be determined in consideration of the area of interest of the subject of examination and other factors.

By making it possible to substitute slit structures with different slits it is also possible to offer a broader range of diagnoses.

There follows a description of a third modification of the first embodiment. This modification relates to the method of interpolation in the interpolation processing unit 29.

Figure 12:
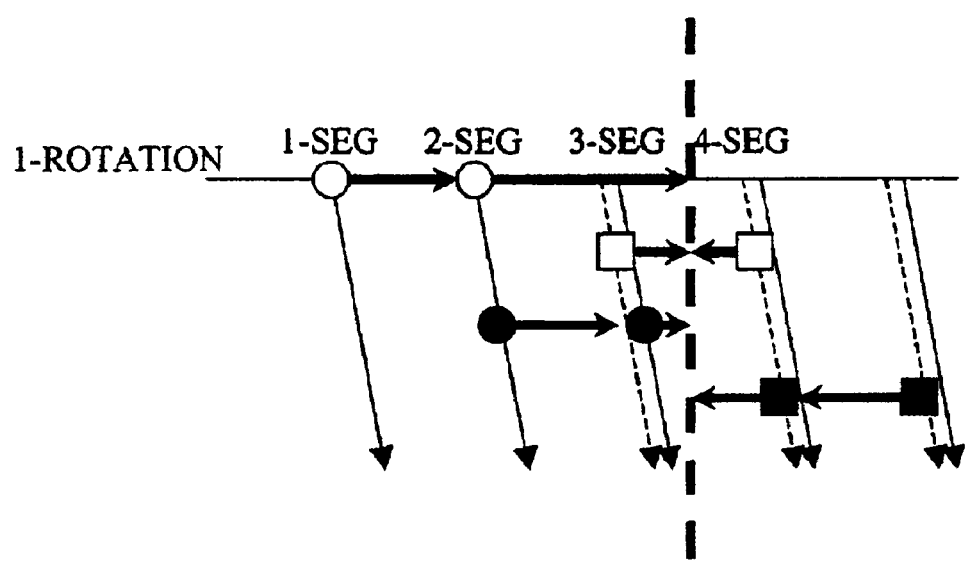
FIG. 12 is a diagram illustrating the collection route for projection data in a third modification of the present invention.

FIG. 12 is a diagram illustrating the collection route for projection data in this modification.

In this modification, projection data (raw data) detected by the detector 23 on the same rotation is selected and used for interpolation, thus creating interpolation data for a prescribed slice surface (shown with a dotted line). As a result, external interpolation (in FIG. 12, interpolation between first and second segment principal data, interpolation between first and second segment QQ data, and interpolation between third and fourth segment QQ data) and internal interpolation (in FIG. 12, interpolation between third and fourth segment principal data) are performed according to the position of the slice surface.

This modification allows a CT image to be created with good resolution even with a reduced number of rotations of the detector by ensuring that at least part of the interpolation according to the position on the slice surface is external.

This has the particular effect of reducing X-ray exposure for the subject of examination.

By enabling external interpolation it is also possible to create interpolation data from projection data detected at the same time (during the same number of rotations), thus making it possible to improve the time resolution of CT images.

There now follows a description of a fourth modification of the first embodiment. This modification relates to the positions of the slits. It should be added that this modification relates particularly to conventional scanning but may also be applied to helical scanning.

Figure 13:
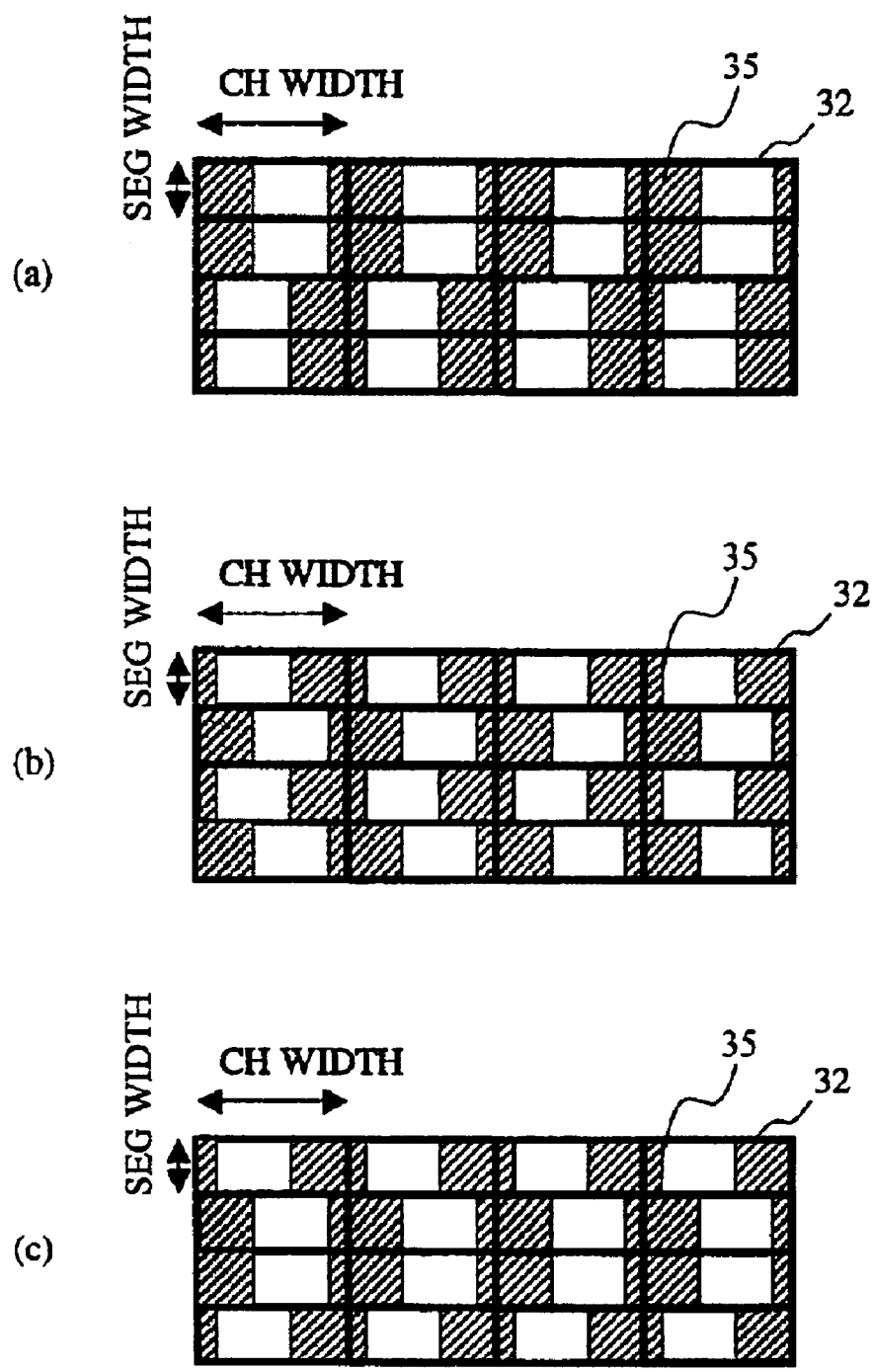
FIGS. 13(a)–13(c) diagrams illustrating the location of slits in a fourth modification of the present invention.

FIGS. 13(a)–13(c) are diagrams illustrating the location of slits in the fourth modification of the present invention. It should be noted that FIG. 13(a) is the same as FIG. 4 relating to the first embodiment. In FIG. 13(b), the alignment positions of the slit structures 35 located on the first segment detection element from the top of the drawing and on the third segment detection element tally (allign) in respect of channel direction, and the same is true of the slit structures 35 located on the second and fourth segment detection elements. Moreover, the alignment positions of the first and second segment detection elements are staggered by ¼ channel width in the channel direction. That is to say, two detection element segments where the alignment position of the slit tallies with the channel direction are located alternately in the segment direction.

In FIG. 13(c) the alignment positions of the slit structures 35 located at the first and fourth segments and at the second and third segments each tally. Moreover, the alignment positions of the first and second segment detection elements are staggered by ¼ channel width in the channel direction. In other words, the alignment positions of the slits tally in the channel direction, while two detection element segments adjacent in the segment direction (the second and third segments in the present modification) are located so that not only do the alignment positions of the slits tally in the channel direction, but they are between the other detection element segments (the first and fourth segments in the present modification).

Figure 14:
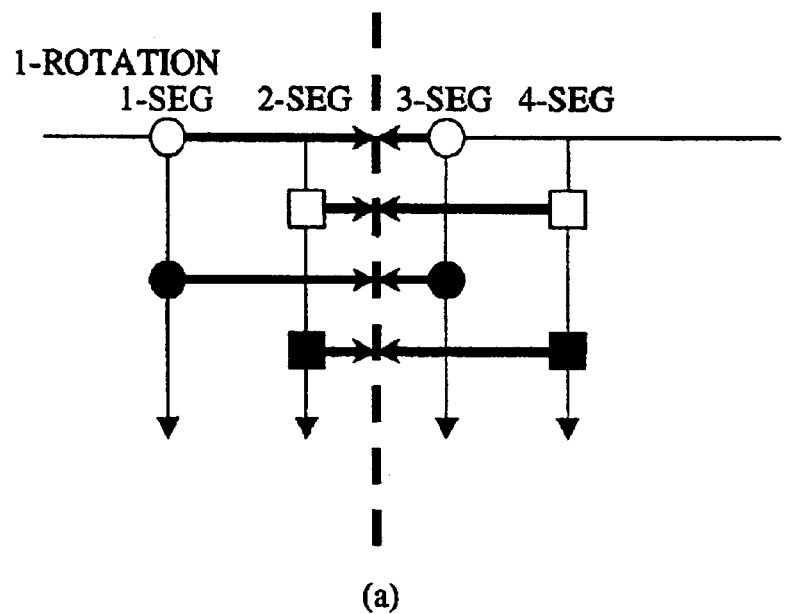
FIGS. 14(a)–14(b) are diagrams illustrating the collection route for projection data in the fourth modification of the present invention.
Figure 14:
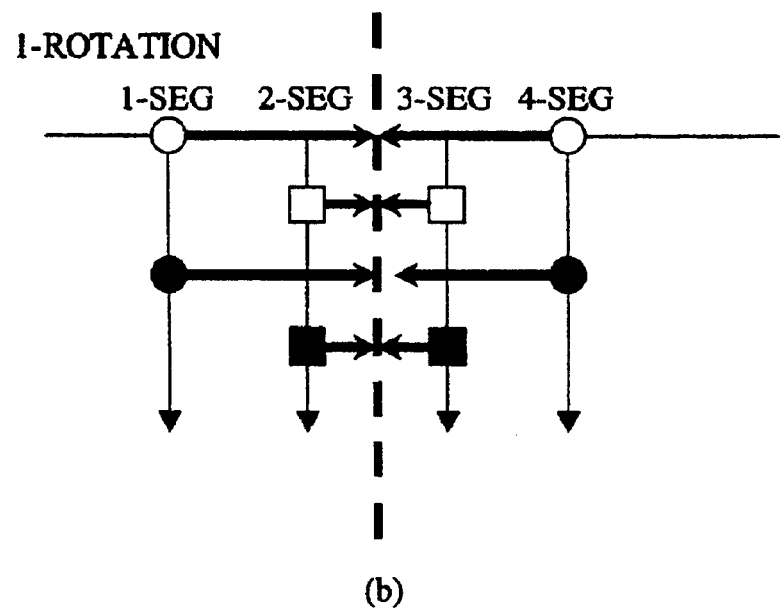

FIG. 14(a) illustrates the collection route for projection data in conventional scanning with a detector having slits as in FIG. 13(b).

If two detection element segments are located in this manner alternately in the segment direction with the alignment positions of the slits tallying in the channel direction, the interpolation data for a prescribed slice surface (between the second and third segments in this case) can be determined entirely by internal interpolation.

In FIG. 13(c) also, if conventional scanning is performed, all the interpolation data in relation to a prescribed slice surface can be created by internal interpolation. FIG. 14(b) illustrates the collection route for projection data in conventional scanning with a detector having slits as in FIG. 13(c). Generally speaking, the distance between projection data in the segment direction is less with internal interpolation than with external, and artifacts do not appear easily.

Moreover, if as illustrated in FIG. 13(b) a detector is used having two detection element segments located alternately in the segment direction with the alignment positions of the slits tallying in the channel direction, interpolation is performed between the first and third segments and between the second and fourth segments, with the result that the distance in the segment direction between projection data used to create interpolation data is at most about two segments in width.

On the other hand, if as illustrated in FIG. 13(c) a detector is used having two detection element segments located so that the alignment positions of the slits tally in the channel direction and they are between other detection element segments, interpolation is performed between the first and fourth segments and between the second and third segments, with the result that the distance in the segment direction between projection data used to create interpolation data is at most about three segments in width.

Accordingly, it is possible to provide a CT image with smaller artifacts by using a detector having two detection element segments located alternately in the segment direction with the alignment positions of the slits tallying in the channel direction, because the distance between the data for interpolation is smaller.

The present modification makes it possible, particularly with conventional scanning, to obtain a CT image of a prescribed slice surface with good resolution by means of internal interpolation in a single rotation of the detector.

Furthermore, it makes it possible to provide a CT image with smaller artifacts by using a detector having two detection element segments located alternately in the segment direction with the alignment positions of the slits tallying in the channel direction.

There follows a description of a fifth modification of the first embodiment. To explain this modification in simple terms, instead of creating slits in the slit structure a plurality of X-ray blocking members is located on the collimator 37.

Figure 15:
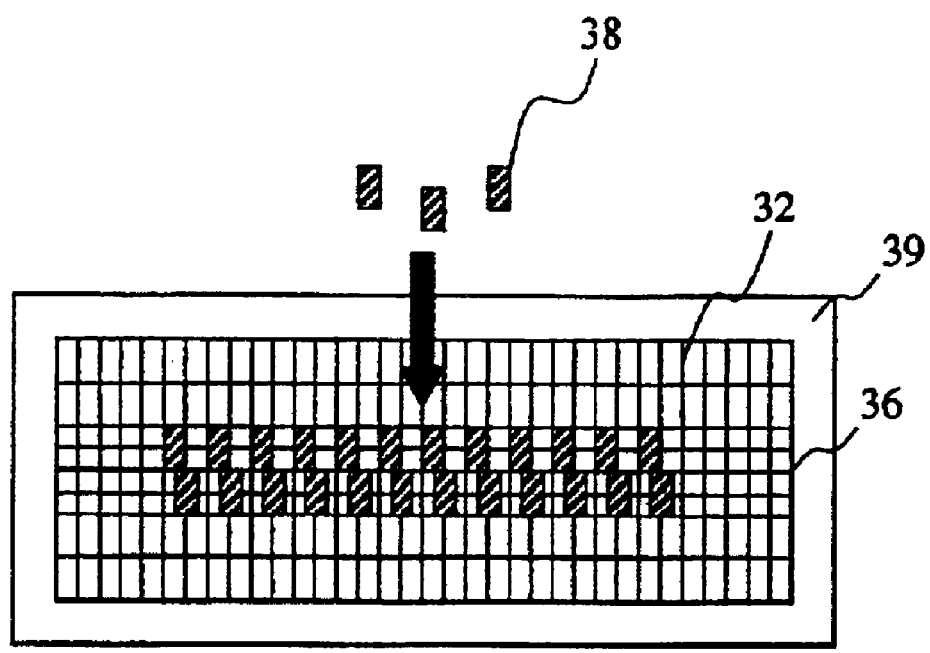
FIG. 15 is a top view of a detector as viewed from the X-ray beam generating source in a fifth modification of the present invention.

FIG. 15 is a top view of a detector in the fifth modification of the present invention. Those parts which are the same as in the first embodiment will be allocated the same reference numeral designations and will not be described again.

The detector in the present modification has a plurality of X-ray blocking members 38 attached with an adhesive agent directly on to a collimator 37 on the X-ray detection element 32 only on four detection element segments with a segment width of 0.5 mm.

The X-ray blocking members 38 are located on the center four detection element segments in the same manner as the slit structures 35 in the first embodiment. It should be added that, as in the case of the slit structures 35, the X-ray blocking members 38 are made of a material with a low X-ray transmission coefficient.

The action of the present modification when a 0.5 mm wide detection element segment is used is the same as in the first embodiment, and will not be explained again.

If detection element segments (segment width 1 mm) other than the center four segments are used, the lack of any members to block X-rays means that it is possible to scan in normal mode (where image reconstruction is performed without insertion of X-ray projection data detected by each detection element) or in QQ mode, which does not use materials to block X-rays.

This modification also makes it possible to provide a CT image with high resolution in the same manner as the first embodiment. Moreover, it requires less in the way of X-ray blocking members than the first embodiment.

There now follows a description of a sixth modification of the first embodiment. To describe this modification in simple terms, the slit structures are divided roughly in the center in the segment direction, and the two sections can be moved outwards from between the X-ray detection element and the X-ray beam generating source.

Figure 16:
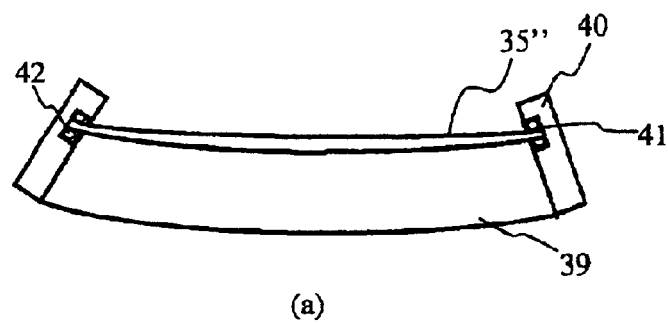
FIG. 16(a)–16(c) are top and front views of a detector as viewed from the X-ray beam generating source in a sixth modification of the present invention.
Figure 16:
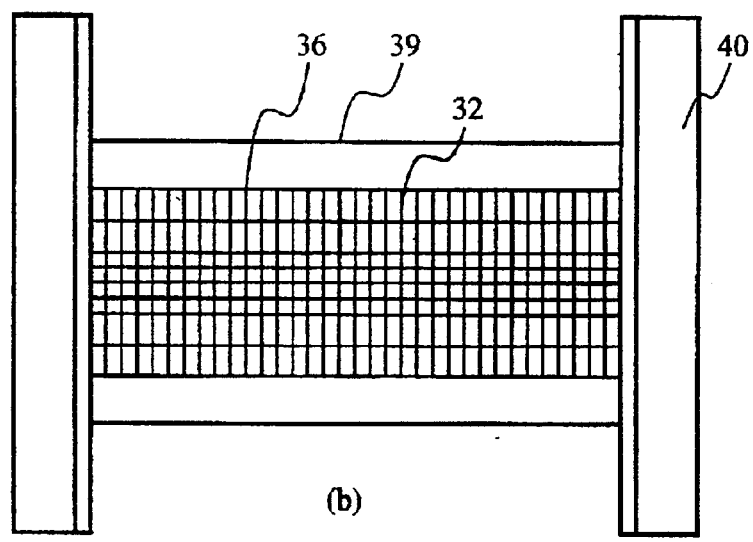
Figure 16:
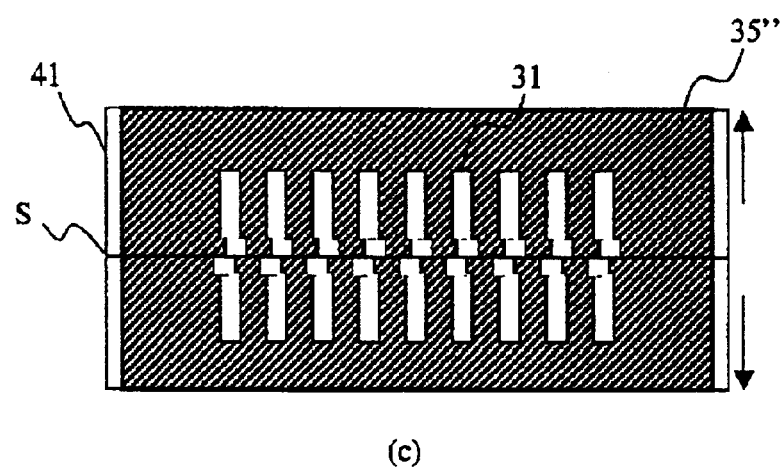

FIGS. 16(a) is a front view and FIGS. 16(b)–16(c) are top views illustrating the detector in this modification as viewed from the X-ray beam generating source. Those parts of the configuration which are the same as in the first embodiment have been allocated the same reference numeral designations, and will not be explained again.

In this modification a slide mechanism 40 is located at the ends of the support unit 39 in the first embodiment in both the channel direction and the opposite direction.

The slide mechanisms 40 are roughly rectangular members extending in the segment direction with one side open, and are fixed to the support unit 39 with their open sides facing one another.

Moreover, slide frames 41 with bearings 42 are located at either end of the slit structures 35" in the channel and opposite directions.

The slit structures 35" have separating surfaces S in the section corresponding to the four center detection element segments (segment width 0.5 mm). These separating surfaces S are positioned so as to divide the four center detection element segments into two sets of two segments each. The separating surfaces S extend to the slide frames 41 located at either end of the slit structures 35".

In other words, the slide frames 41 are also divided by the separating surfaces S into a section in the segment direction and one in the opposite direction (represented by arrows).

It should be pointed out that since unlike the first embodiment it is necessary for the slit structures 34" to move, there are no screw holes 33 or screw grooves 33'.

To explain the action of this modification, the operator can select normal mode in addition to QQ mode and high-resolution mode. By normal mode is meant a mode in which images are reconstructed without inserting X-ray projection data detected by each of the other detection elements.

If the operator selects normal mode, the slide frames 41 pass along the grooves of the slide mechanisms 40 in accordance with a signal from a slit structure divide controller (not depicted in the drawing), and the slit structures 35" move in the segment direction and in the opposite direction (shown by arrows) respectively.

In this manner the slit structures 35" located between the X-ray detection element and the X-ray beam generating source move outwards from that location. This means that in normal mode the image is reconstructed in accordance with projection data detected by each detection element without the X-rays being blocked by the slit structures 35".

If the operator selects QQ mode or high-resolution mode, the action is the opposite, and the slit structures 35" move between the X-ray detection element and the X-ray beam generating source. Explanations of QQ mode and high-resolution mode as such will be omitted here.

In addition to being able to provide CT images with good resolution, this modification makes it possible to use normal mode as well as QQ mode and high-resolution mode, making it possible to create CT images according to the needs of the diagnosis.

It should be added that this is not confined to the present modification, but there is no need to move the slit structures for all the detection element segments outwards, and it is sufficient to move those from between the X-ray beam generating source and the detection element segments which are being used.

There follows a description of a seventh modification of the first embodiment. To explain this modification in simple terms, the slit structures are not divided roughly in the center in the segment direction, but can be moved outwards as a whole from between the X-ray detection element and the X-ray beam generating source.

Those parts of the configuration which are the same as in the first embodiment have been allocated the same reference numeral designations, and will not be explained again.

Figure 18:
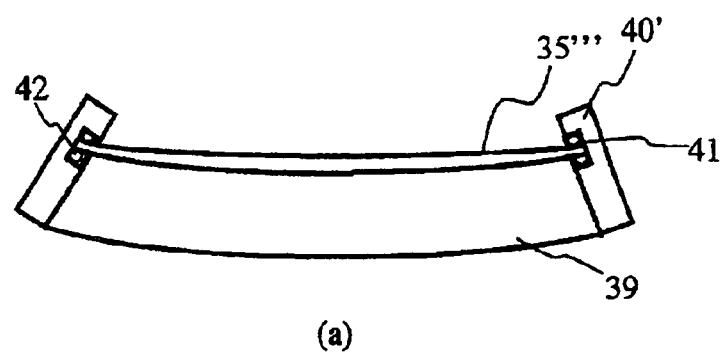
FIGS. 18(a)–18(c) are top view illustrating the detector in the present modification as viewed from the X-ray beam generating source.
Figure 18:
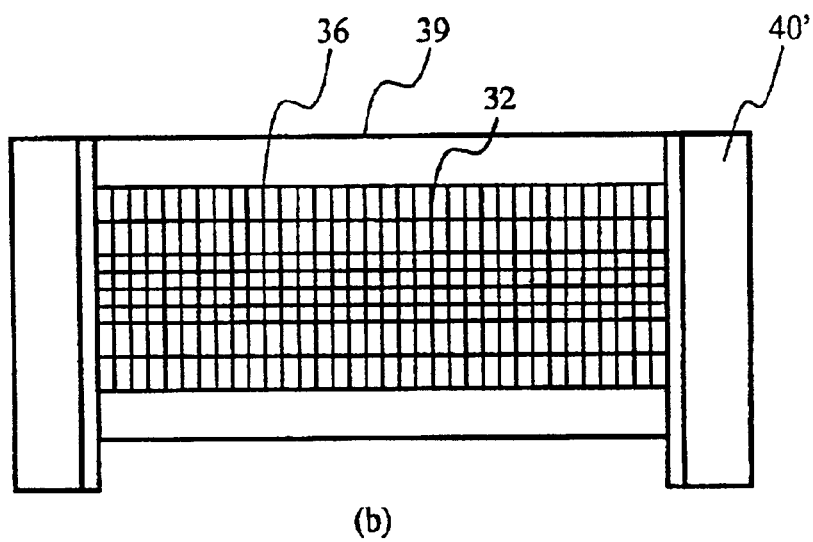
Figure 18:
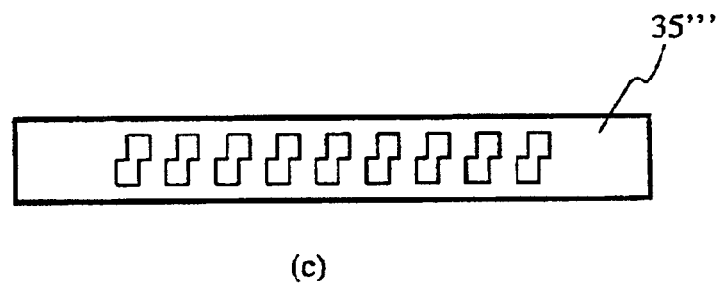

FIG. 18(a) is a front view, and FIGS. 18(b)–18(c) are top views illustrating the detector in the present modification as viewed from the X-ray beam generating source. Those parts of the configuration which are the same as in the first embodiment have been allocated the same reference numeral designations, and will not be explained again.

Slide mechanisms 40' are provided at the ends of the support unit 39 in both the channel direction and the opposite direction in the present modification as in the sixth modification.

The slide mechanisms 40' are roughly rectangular members extending in the segment direction with one side open, and are fixed to the support unit 39 with their open sides facing one another.

Moreover, slide frames 41 with bearings 42 are located at either end of the slit structures 35''' in the channel and opposite directions, and the slide frames 41 are fitted into grooves in the slide mechanisms 40'. The bearings 42 are attached in a direction which allows the slide frame 41 to move along the groove of the slide mechanism 40' in the segment direction. The slit structures 35''' have slits only in the section corresponding to the center four detection element segments (segment width 0.5 mm) of the detector. The width of the slit structures 35''' in the segment direction is less than the added segment widths of each of the detection elements 32 arranged in the segment direction.

Figure 19:
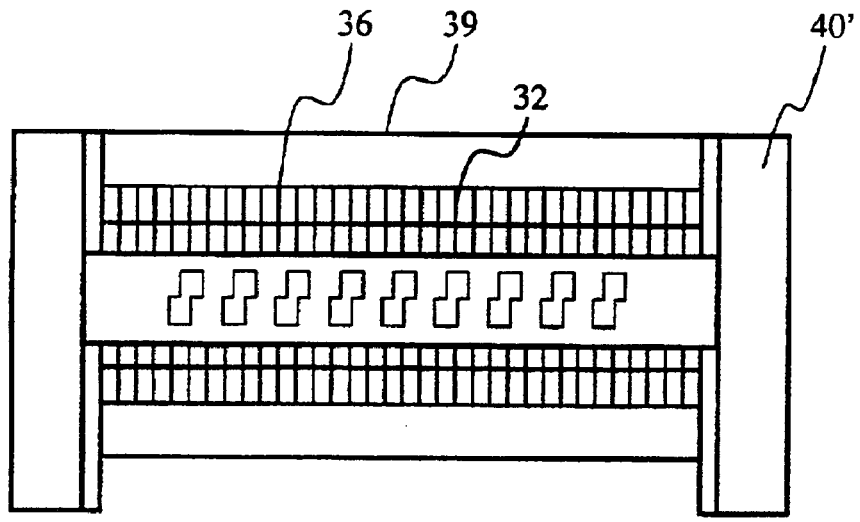
FIG. 19(a) is a top view of an X-ray detector according to one aspect of the present invention in a high-resolution mode.
FIG. 19(b) is a top view of the X-ray detector in a normal mode.
Figure 19:
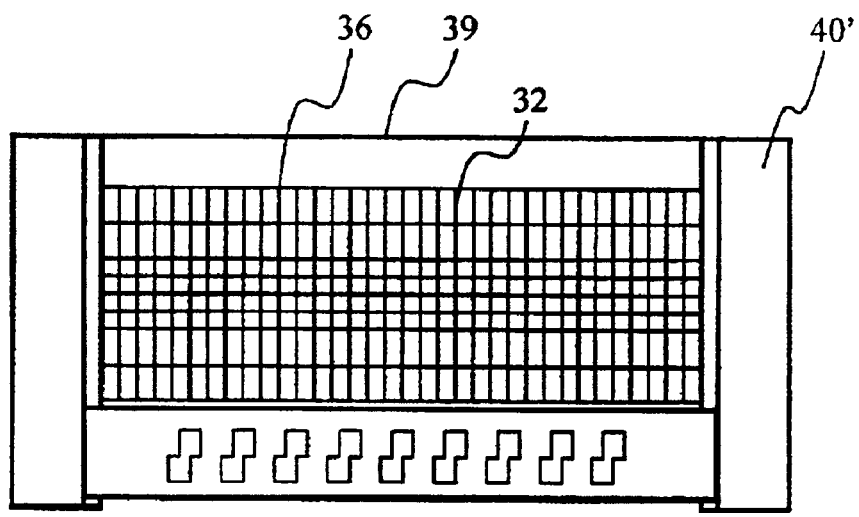

To explain the action of the present modification, the operator can select normal mode in addition to QQ mode and high-resolution mode. If the operator selects normal mode, the slit structures 35''' pass along the grooves of the slide mechanisms 40 in accordance with a signal from a slit structure divide controller, and move in the segment direction. Accordingly, in normal mode the image is reconstructed in accordance with projection data detected by each of the detection elements without the X-rays being blocked by the slit structure 35'''. If the operator selects high-resolution mode, the opposite occurs, which is to say the slit structures 35''' move between the X-ray detection elements and the X-ray beam generating source. FIG. 19(*a*) is a top view of the detector 36 in high-resolution mode, while FIG. 19(*b*) is a top view of the detector in normal mode.

In addition to being able to provide CT images with good resolution, this modification makes it possible to use normal mode as well as QQ mode and high-resolution mode, making it possible to create CT images according to the needs of the diagnosis.

There now follows, with reference to the drawings, a description of the second embodiment of the present invention. Those parts of the configuration which are the same as in the first embodiment have been allocated the same codes, and will not be explained again.

Figure 17:
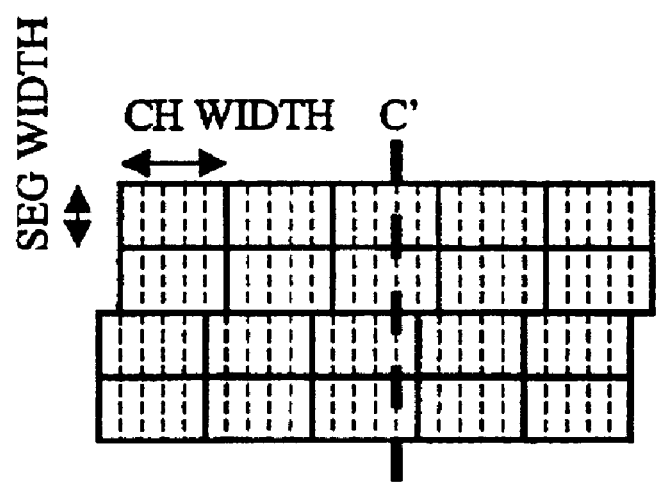
FIG. 17 is a top view of an X-ray detector in a second embodiment of the present invention.

FIG. 17 is a top view of the X-ray detector 23' in the present embodiment. In order to simplify the explanation, the detection element has been shown as four segments by five channels. In actual fact it comprises 34 segments by 900 channels as in the first embodiment.

Moreover, there is thin dotted line in FIG. 17 at roughly every ⅕ CH width of the detection element. This is to clarify the arrangement of the detection element.

The X-ray detector 23' of the present embodiment has a plurality of detection elements arranged in the channel and segment directions. Of these detection elements, the alignment of a plurality of detection element segments (two segments at the top of FIG. 17) tallies in the channel direction, while a prescribed number of detection element segments (two segments at the bottom of FIG. 17) are staggered in the channel direction and opposite direction in relation to the top two detection element segments. The extent of this staggering is ⅕ CH width of the detection element.

The rotation-centered projection axis of the detector 23' is staggered a further ⅕ CH width in the channel and opposite directions in comparison with the bottom two detection element segments.

This configuration means that principal data detected in the first and second segments, principal data detected in the third and fourth segments, QQ data detected in the first and second segments and QQ data detected in the third and fourth segments are the same as in the first embodiment, and each of the QQ data corresponds to data between each of the principal data.

Other details of the configuration and action will not be explained here because they are roughly the same as in the first embodiment.

This embodiment also makes it possible to provide a CT image with good resolution.

With this embodiment there is no need to have a slit structure, and a CT image with good resolution can be provided by staggering the detection elements in the channel direction, making it easier to manufacture the detector.

The above is a description of the embodiments and modifications of the present invention, but other combinations are possible. For instance, in the first embodiment it is possible to stagger only the slits without staggering the positions of the detection elements, and in the second embodiment instead of staggering the positions of the detection elements without providing slits it is possible to stagger the positions of the detection elements and use a slit structure with staggered slits.

The description in the embodiments and modifications has centered on internal and external interpolation with two types of projection data for every prescribed angle of rotation in relation to prescribed slice surfaces, but internal and external interpolation from three or more types of projection data may also be employed, as may combinations of internal and external interpolation.

Likewise, the description has centered on four-segment detection elements with a segment width of 0.5 mm in the vicinity of the center of the detector and detection element segments with segment widths of 1 mm in the segment and opposite directions, but it is also possible to use just detection element segments with roughly the same segment width.

The embodiments have centered on so-called third-generation devices where the X-ray tube and detector rotate in synchronization, but it is possible to adopt other generations of CT apparatus. For example, the invention can be adapted to a so-called fourth-generation CT apparatus with the detector fixed in a the shape of a ring. Similarly, it may also be adapted to a so-called fifth-generation electron beam CT apparatus, which dispenses with an X-ray tube.

The above explanation has assumed that the collimator and slits are configured separately, but they may constitute a single body.

The explanation has centered on reconstructing slice surfaces perpendicular to the direction of the body axis, but it is possible to create other cross-sectional surface images.

The explanation has also centered on short slits for use as apertures for detecting X-rays, but for reasons relating to manufacture they may also be other shapes (e.g., round shapes).

It is also possible to provide X-ray blocking members controlling the width of the X-ray beam so that X-rays are incident only on the area where the detector slit on the X-ray beam generating source side rather than the subject of examination side, i.e., with the subject disposed between the blocking members and the X-ray detector. In this manner it is possible to inhibit X-rays incident on the subject of examination.

Finally, the above embodiments and modifications have assumed that the relative positions of the subject of examination and the detector are changed by moving the bed, but it is also possible to do so by moving the frame on which the detector is located.

Numerous modifications and variations of the present invention are possible in light of the above teachings. It is therefore to be understood that within the scope of the appended claims, the invention may be practiced otherwise than as specifically described herein.

What is claimed is:

1. An X-ray CT apparatus, comprising:
   an X-ray source configured to generate X-rays towards a subject;
   a rotation mechanism configured to rotate the X-ray source around a rotational axis;
   an X-ray detector having a plurality of detection elements arranged in a first direction roughly parallel to the rotational axis and in a second direction which is different from the first direction and configured to detect X-rays emitted from the X-ray source;
   a blocking member located between the X-ray source and the X-ray detector and configured to block X-rays;
   a reconstruction unit configured to reconstruct an image of the subject in accordance with the data detected by the X-ray detector; and
   the blocking member comprising an aperture including a first section and a second section, the second section located in the first direction in relation to the first section and staggered in relation to the first section in the second direction;
   wherein a plurality of apertures is located at prescribed intervals in the second direction;
   wherein the rotational axis is arranged such that a line projecting the rotational axis from the X-ray source on to the X-ray detector is staggered in the second direction in relation to an alignment-centered axis of the X-ray detector;
   wherein the line projecting the rotational axis is staggered by roughly ¼ the width of the detection element in the second direction,
   the first section of the aperture is staggered by roughly ¼ the width of the detection element in the second direction in relation to the second section of the aperture,
   the center of the second section of the aperture is staggered by roughly ⅜ the width of the detection element in the second direction in relation to the alignment-centered axis, and
   the widths of the first section and the second section are roughly ½ detection element, respectively, in the second direction.

2. An X-ray CT apparatus comprising:
   an X-ray source configured to generate X-rays towards a subject;
   a rotation mechanism configured to rotate the X-ray source around a rotational axis;
   an X-ray detector having a plurality of detection elements arranged in a first direction roughly parallel to the rotational axis and in a second direction which is different from the first direction and configured to detect X-rays emitted from the X-ray source;
   a blocking member located between the X-ray source and the X-ray detector and configured to block X-rays;
   a reconstruction unit configured to reconstruct an image of the subject in accordance with the data detected by the X-ray detector; and
   the blocking member comprising an aperture including a first section and a second section, the second section located in the first direction in relation to the first section and staggered in relation to the first section in the second direction;
   wherein a plurality of apertures is located at prescribed intervals in the second direction;
   wherein the rotational axis is arranged such that a line projecting the rotational axis from the X-ray source on to the X-ray detector is staggered in the second direction in relation to an alignment-centered axis of the X-ray detector;
   wherein the line projecting the rotational axis is staggered by roughly ⅛ the width of the detection element in the second direction,
   the first section of the aperture is staggered by roughly ½ the width of the detection element in the second direction in relation to the second section of the aperture,
   the center of the second section of the aperture is staggered by roughly ¼ the width of the detection element in the second direction in relation to the alignment-centered axis, and
   the widths of the first section and the second section are roughly ½ detection element, respectively, in the second direction.

3. An X-ray CT apparatus comprising:
   an X-ray source configured to generate X-rays towards a subject;
   a rotation mechanism configured to rotate the X-ray source around a rotational axis;
   an X-ray detector having a plurality of detection elements arranged in a first direction roughly parallel to the rotational axis and in a second direction which is different from the first direction and configured to detect X-rays emitted from the X-ray source;
   a blocking member located between the X-ray source and the X-ray detector and configured to block X-rays;
   a reconstruction unit configured to reconstruct an image of the subject in accordance with the data detected by the X-ray detector; and
   the blocking member comprising an aperture including a first section and a second section, the second section located in the first direction in relation to the first section and staggered in relation to the first section in the second direction;
   wherein a plurality of apertures is located at prescribed intervals in the second direction;
   wherein the rotational axis is arranged such that a line projecting the rotational axis from the X-ray source on to the X-ray detector is staggered in the second direction in relation to an alignment-centered axis of the X-ray detector;
   a movement mechanism configured to move the blocking member inwards between the X-ray detection elements and the X-ray source, or outwards from between the X-ray detection elements and the X-ray source.

4. An X-ray CT apparatus comprising:
   an X-ray source configured to generate X-rays towards a subject;
   a rotation mechanism configured to rotate the X-ray source around a rotational axis;
   an X-ray detector having a plurality of detection elements arranged in a first direction roughly parallel to the rotational axis and in a second direction which is different from the first direction and configured to detect X-rays emitted from the X-ray source;

a blocking member located between the X-ray source and the X-ray detector and configured to block X-rays;

a reconstruction unit configured to reconstruct an image of the subject in accordance with the data detected by the X-ray detector; and the blocking member comprising an aperture including a first section and a second section, the second section located in the first direction in relation to the first section and staggered in relation to the first section in the second direction;

wherein a plurality of apertures is located at prescribed intervals in the second direction;

wherein the rotational axis is arranged such that a line projecting the rotational axis from the X-ray source on to the X-ray detector is staggered in the second direction in relation to an alignment-centered axis of the X-ray detector;

a movement mechanism configured to move the blocking member inwards between the X-ray detection elements and the X-ray source, or outwards from between the X-ray detection elements and the X-ray source;

wherein the blocking member is at least partially divisible.

5. An X-ray CT apparatus comprising:

an X-ray source configured to generate X-rays towards a subject;

a rotation mechanism configured to rotate the X-ray source around a rotational axis;

an X-ray detector having a plurality of detection elements arranged in a first direction roughly parallel to the rotational axis and in a second direction which is different from the first direction and configured to detect X-rays emitted from the X-ray source;

a reconstruction unit configured to reconstruct an image of the subject in accordance with the data detected by the X-ray detector; and the X-ray detector comprising at least four detection elements in the first direction, at least two detection elements being arranged aligned in relation to the second direction, and at least two detection elements being staggered against the at least two aligned X-ray detection elements in relation to the second direction.

6. An X-ray CT apparatus according to claim 5, wherein the rotational axis is arranged such that a line projecting it from the X-ray source on to the X-ray detector is staggered in the second direction in relation to an alignment-centered axis of the X-ray detector.

7. An X-ray CT apparatus comprising:

an X-ray source configured to generate X-rays towards a subject;

a rotation mechanism configured to rotate a focal point of an X-ray emitted from the X-ray source around a rotational axis;

an X-ray detector having a first detection segment and a second detection segment staggered with respect to the first detection segment in relation to a channel direction, each of said detection segments including a plurality of detection elements extending in a channel direction;

an interpolation processing unit configured to perform helical interpolation using a first and second projection data detected by the first and the second detection segments in a first position of the focal point of the X-ray, and third and fourth projection data detected by the first and the second detection segment in a second position where the focal point of the X-ray is roughly half a rotation from the first position; and a reconstruction unit configured to reconstruct an image of the subject in accordance with the interpolated data.

* * * * *